United States Patent
Meacci et al.

(10) Patent No.: US 12,357,622 B2
(45) Date of Patent: Jul. 15, 2025

(54) PHARMACEUTICAL COMPOSITION OF S1PR MODULATORS

(71) Applicant: UNIVERSITA DEGLI STUDI DI FIRENZE, Florence (IT)

(72) Inventors: Elisabetta Meacci, Florence (IT); Federica Pierucci, Pistoia (IT)

(73) Assignee: UNIVERSITA DEGLI STUDI DI FIRENZE, Florence (IT)

( * ) Notice: Subject to any disclaimer, the term of this patent is extended or adjusted under 35 U.S.C. 154(b) by 869 days.

(21) Appl. No.: 17/620,879

(22) PCT Filed: Jul. 29, 2020

(86) PCT No.: PCT/IB2020/057144
§ 371 (c)(1),
(2) Date: Dec. 20, 2021

(87) PCT Pub. No.: WO2021/024101
PCT Pub. Date: Feb. 11, 2021

(65) Prior Publication Data
US 2022/0313672 A1    Oct. 6, 2022

(30) Foreign Application Priority Data

Aug. 2, 2019  (IT) ................. 102019000013890

(51) Int. Cl.
| | | |
|---|---|---|
| *A61K 31/661* | (2006.01) | |
| *A61K 31/155* | (2006.01) | |
| *A61K 31/164* | (2006.01) | |
| *A61K 31/40* | (2006.01) | |
| *A61K 31/4439* | (2006.01) | |
| *A61K 31/662* | (2006.01) | |
| *A61K 31/7088* | (2006.01) | |
| *A61P 21/00* | (2006.01) | |
| *C12N 15/113* | (2010.01) | |

(52) U.S. Cl.
CPC ........ *A61K 31/4439* (2013.01); *A61K 31/155* (2013.01); *A61K 31/661* (2013.01); *A61P 21/00* (2018.01); *C12N 15/113* (2013.01); *C12N 2310/14* (2013.01)

(58) Field of Classification Search
CPC .............. A61K 31/4439; A61K 31/661; A61K 31/165; A61K 31/40; A61K 31/662; A61K 31/7088; A61P 21/00
See application file for complete search history.

(56) References Cited

U.S. PATENT DOCUMENTS

2006/0094790 A1    5/2006  Park et al.

FOREIGN PATENT DOCUMENTS

WO    2012097330 A2    7/2012

OTHER PUBLICATIONS

Pierucci et al., Involvement of released sphingosine 1-phosphate/sphingosine 1-phosphate receptor axis in skeletal muscle atrophy, Biochimica et Biophysica Acta (BBA)—Molecular Basis of Disease, vol. 1864, Issue 12, pp. 3598-3614. (Year: 2018).*
Liu et al., Conjugated Bile Acids Promote Invasive Growth of Esophageal Adenocarcinoma Cells and Cancer Stem Cell Expansion via Sphingosine 1-Phosphate Receptor 2-Mediated Yes-Associated Protein Activation, The American Journal of Pathology, vol. 188, Issue 9, pp. 2042-2058. (Year: 2018).*
International Search Report and Written Opinion for Corresponding International Application No. PCT/IB2020/057144 1 (11 Pages) (Nov. 10, 2020).

* cited by examiner

Primary Examiner — Abigail Vanhorn
(74) Attorney, Agent, or Firm — LUCAS & MERCANTI, LLP

(57) ABSTRACT

The present invention relates to a pharmaceutical composition useful in the prevention and treatment of atrophy or of degeneration of skeletal muscle caused by pathologies or of sarcopenia. The composition includes a combination of molecules that are modulators of the sphingosine-1-phosphate receptors S1PR and one or more pharmaceutically acceptable excipients and/or carriers.

9 Claims, 19 Drawing Sheets
Specification includes a Sequence Listing.

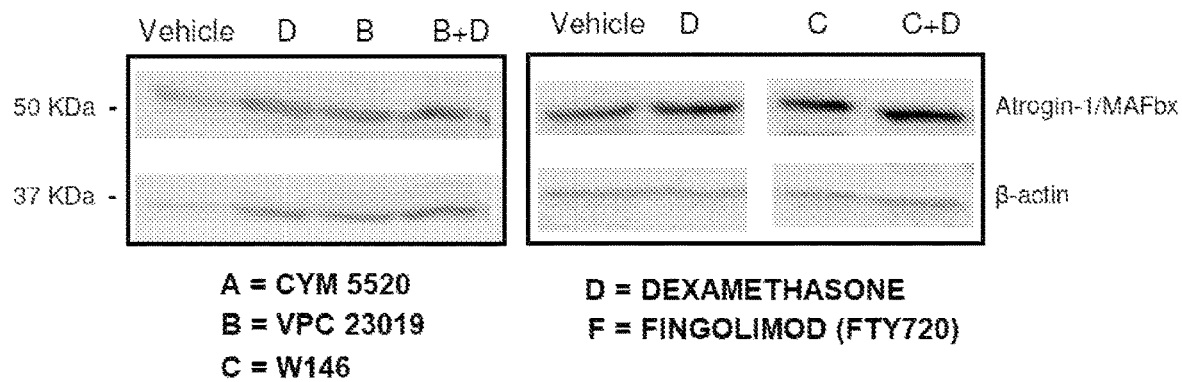
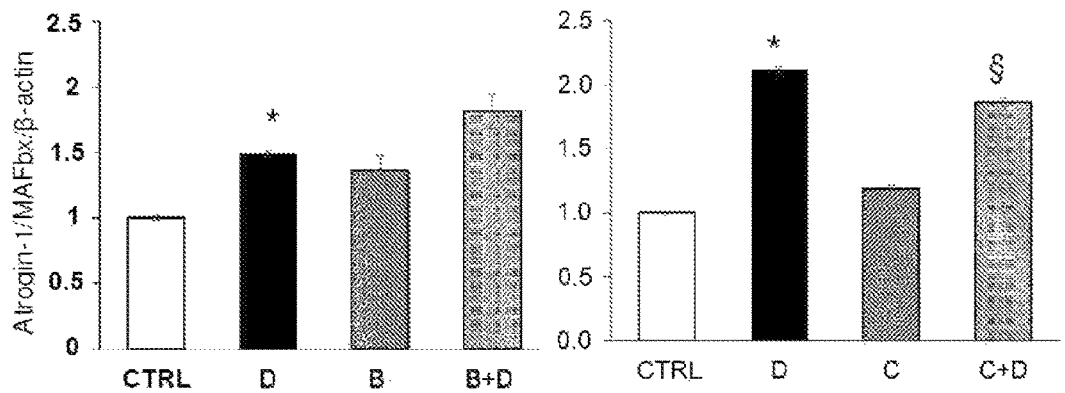
Fig. 2B
Fig. 2C
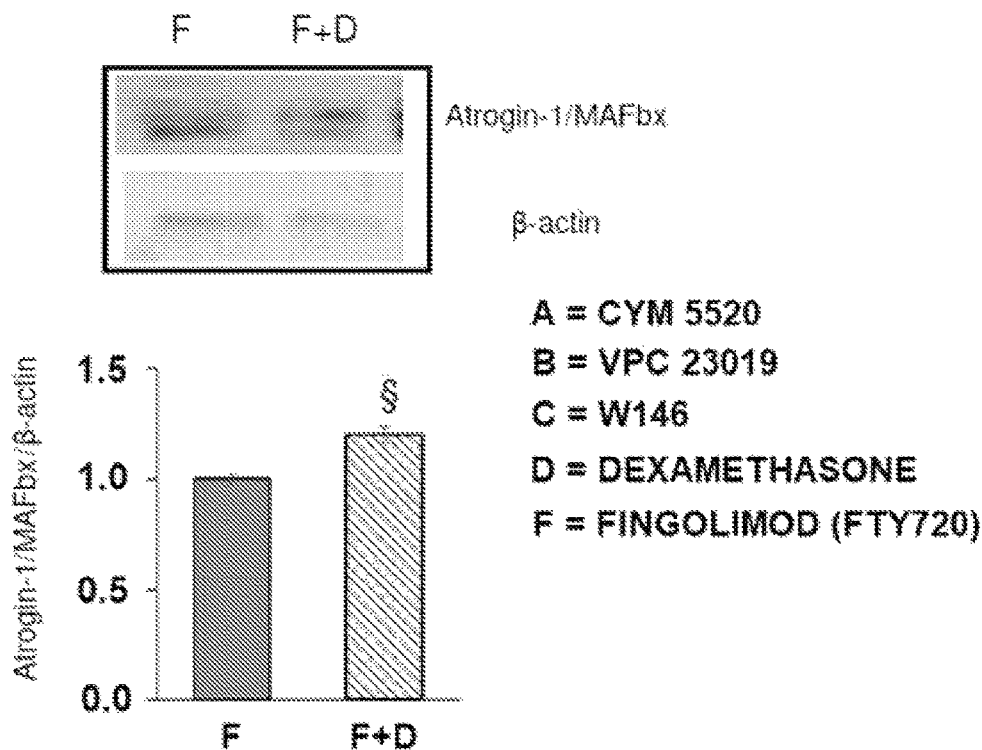
A = CYM 5520
B = VPC 23019
C = W146
D = DEXAMETHASONE
F = FINGOLIMOD (FTY720)
Fig. 2D

B= VPC 23019
C= W146
D= DEXAMETHASONE

B= VPC 23019
C= W146
D= DEXAMETHASONE

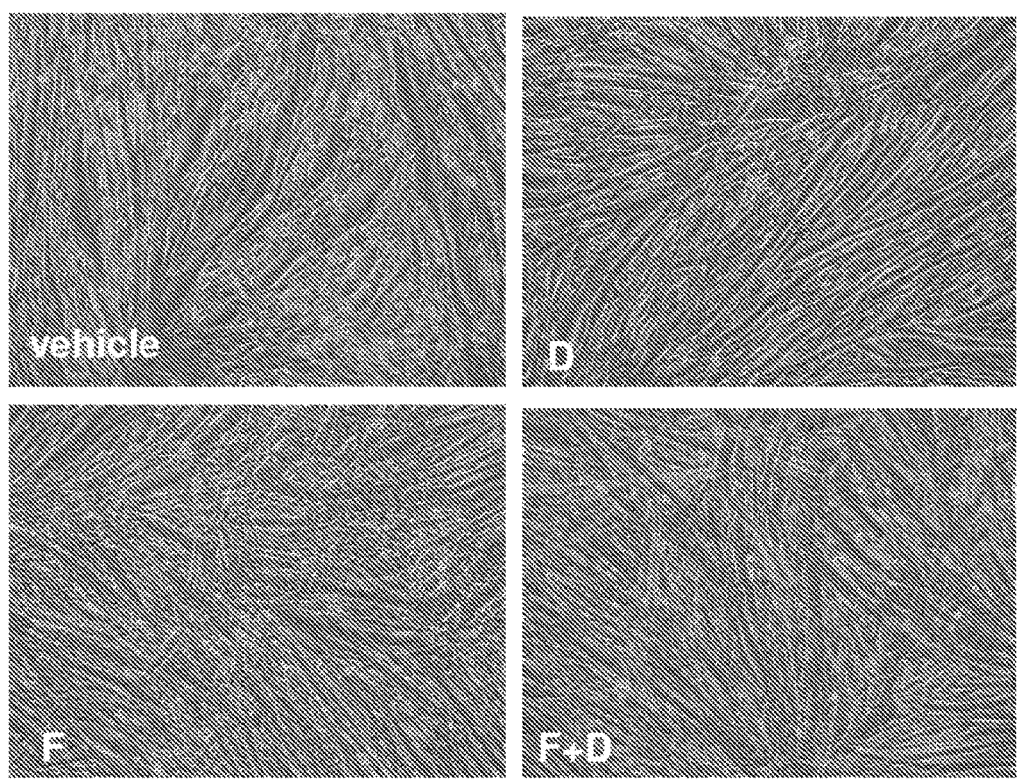
D = DEXAMETHASONE    B = VPC 23019    C = W146
Fig. 3C
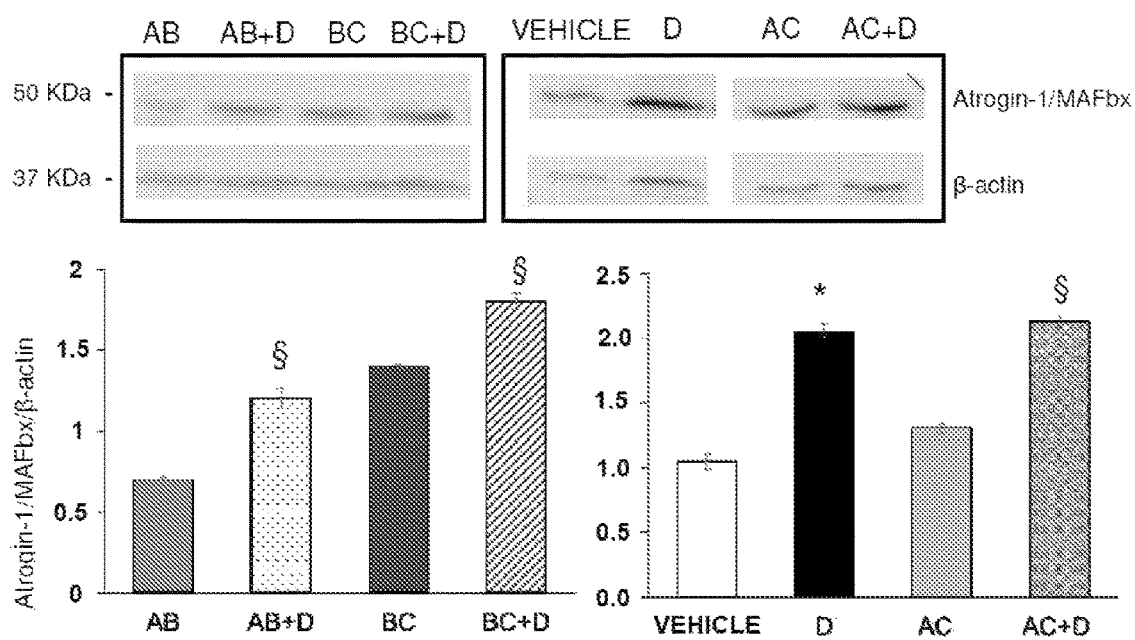
A= CYM 5520    B= VPC 23019    C= W146    D= DEXAMETHASONE
Fig. 4A                                    Fig. 4B

A= CYM 5520  B= VPC 23019  C= W146  D= DEXAMETHASONE

A= CYM 5520
B= VPC 23019
C= W146
D= DEXAMETHASONE

B= VPC 23019   C= W146   D= DEXAMETHASONE

A= CYM 5520
B= VPC 23019
C= W146
D= DEXAMETHASONE

A= CYM 5520    B= VPC 23019    C= W146    D= DEXAMETHASONE

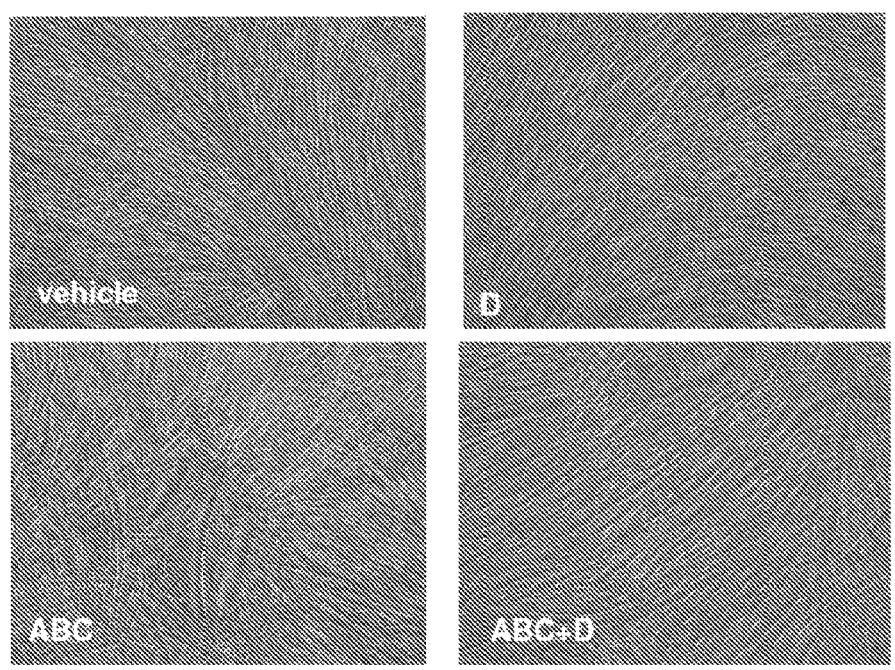
A= CYM 5520  B= VPC 23019  C= W146  D= DEXAMETHASONE
at 24 h incubation
Fig. 7B
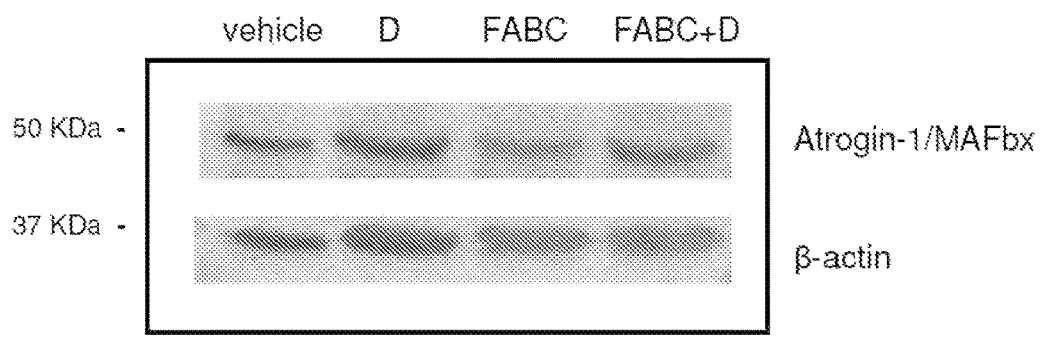
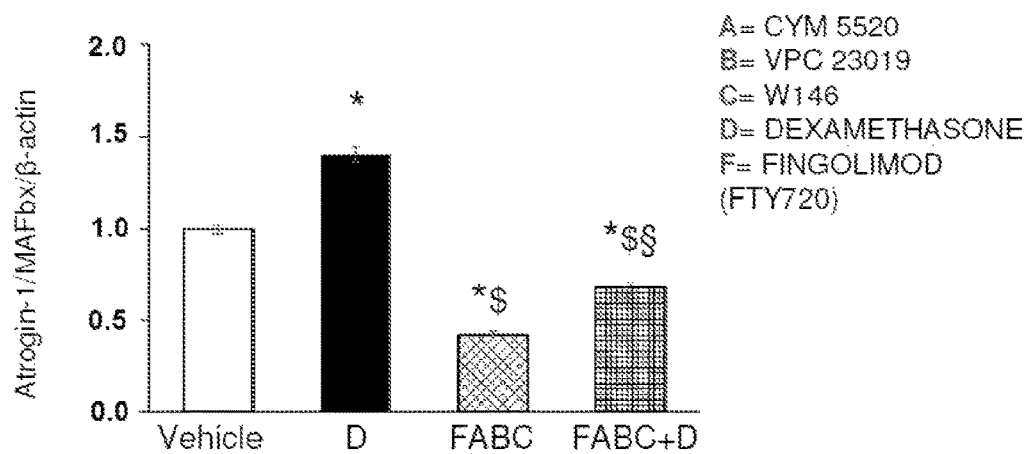
A= CYM 5520
B= VPC 23019
C= W146
D= DEXAMETHASONE
F= FINGOLIMOD
(FTY720)
Fig. 8

A-ATROFI= 2:1:2    MIX I= 1:1:1+D    MIX II= 1:0.5:1+D

MIX III = 0.5:0.5:0.5+D    MIX IV= 0.5:0.25:0.5+D

D= DEXAMETHASONE

A-ATROFI = CYM 5520 + VPC 23019 + W146

MIX III = 0.5:0.5:0.5+D
MIX IV = 0.5:0.25:0.5+D
MIX V = 0.1:0.05:0.1+D
MIX VI = 2:1:1+D
MIX VII = 3:2:3+D
MIX VIII = 5:4:5+D
D = DEXAMETHASONE

D = DEXAMETHASONE

A-ATROFI = CYM 5520 + VPC 23019 + W146

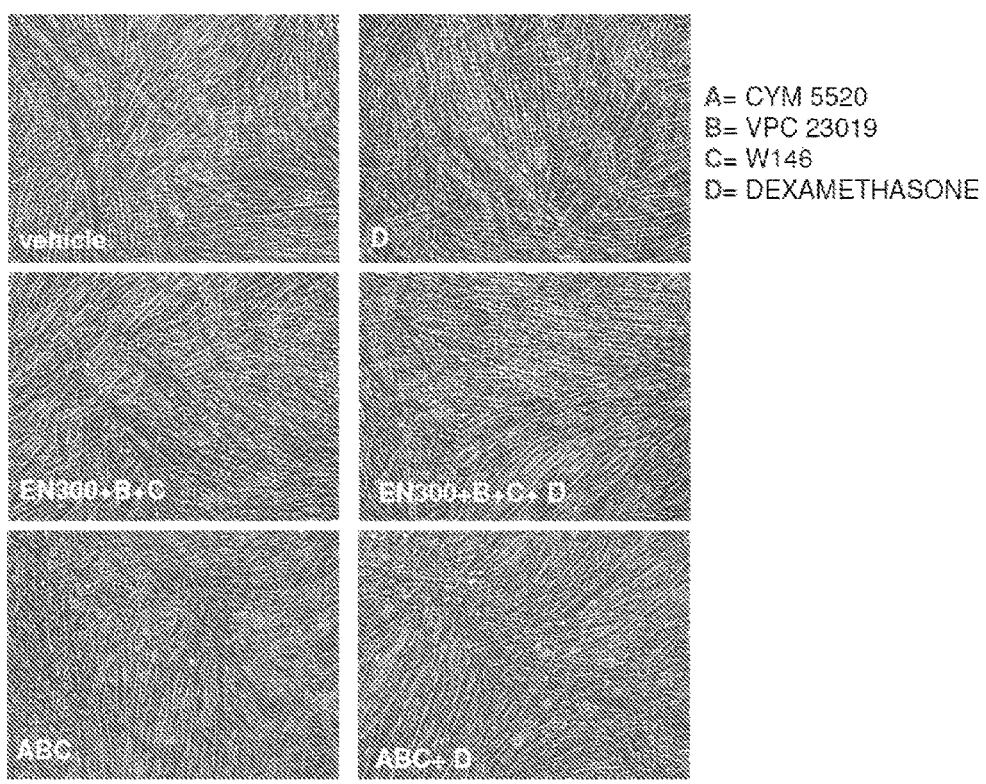
A = CYM 5520
B = VPC 23019
C = W146
D = DEXAMETHASONE
Fig. 11C
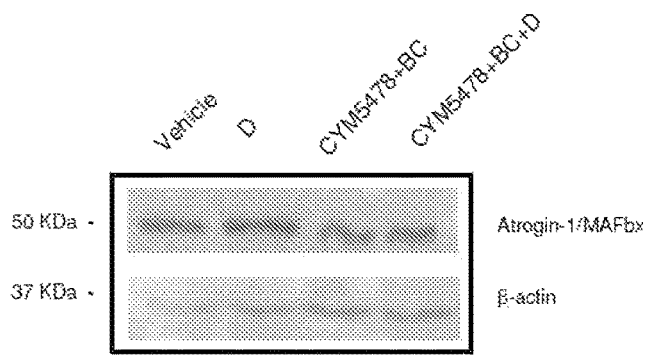
B = VPC 23019
C = W146
D = DEXAMETHASONE
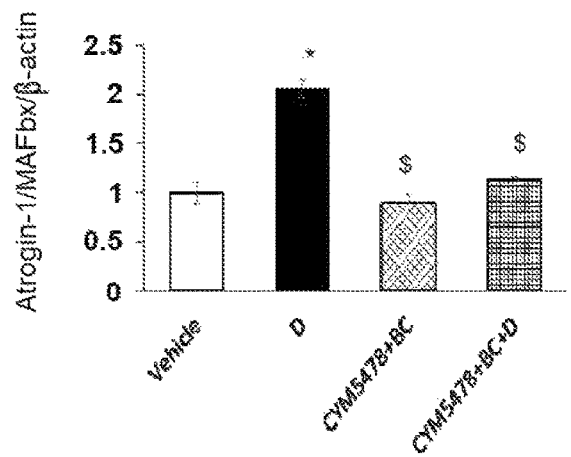
Fig. 12A

B = VPC 23019   C = W146   D = DEXAMETHASONE

A = CYM 5520
C = W146
TY = TY52156
D = DEXAMETHASONE
A-ATROFI = CYM 5520 + VPC 23019 + W146

A= CYM 5520  C= W146  D= DEXAMETHASONE
SCR= Scramble  SiRNA-S1PR3

A= CYM 5520  C= W146  SCR= Scramble  S1PR3-siRNA  D= DEXAMETHASONE

A= CYM 5520   B= VPC 23019   C= W146   D= DEXAMETHASONE

A= CYM 5520    B= VPC 23019    C= W146    D= DEXAMETHASONE

A= CYM 5520   B= VPC 23019   C=W146   D= DEXAMETHASONE

PHARMACEUTICAL COMPOSITION OF S1PR MODULATORS

CROSS-REFERENCE TO RELATED APPLICATIONS

This application is a 371 of PCT/IB2020/057144, filed Jul. 29, 2020, which claims the benefit of Italian Patent Application No. 102019000013890, filed Aug. 2, 2019.

FIELD OF THE INVENTION

The present invention relates in general to the pharmaceutical field, and more precisely it refers to a pharmaceutical composition of modulators of sphingosine-1-phosphate receptors (S1PR), useful in the treatment and in the prevention of sarcopenia, and of atrophy or degeneration of skeletal muscle, associated to pathologies

STATE OF THE ART

Skeletal muscle (SkM) represents the largest "organ" in the human body, as it constitutes at least 40% of the body mass and contains 50-75% of all proteins in the human body (Frontera, W R and Ochala, *J. Calcif. Tissue Int.* (2015)). The musculoskeletal tissue is essential for the health and locomotion of people, and its weakening with wasting muscle mass is associated with a significant reduction in independence, quality and life expectancy.

The state of degeneration of the musculoskeletal tissue (skeletal muscle wasting (MW)) is a serious condition, whether of physiological or pathological origin. In aging, a degeneration of skeletal muscle can be observed, which is generically called "sarcopenia". The most recurrent pathological conditions associated with MW are dystrophy, cancer, sepsis, hepatic cirrhosis, heart failure, and kidney and lung failure.

Pathological skeletal muscle degeneration significantly worsens the prognosis of the diseases associated to it, increases the morbidity and suffering of patients, with an incidence of 10-50% in cancer patients and of 20-60% in patients suffering of chronic infection. Starvation, disuse, primary depression due to prolonged immobilization, malabsorption and hyperthyroidism can be included in the list of factors related to the loss of musculoskeletal mass.

Currently, no drug treatment is available for muscle degeneration, so exercise and ample intake of proteins, vitamins and supplements are the only interventions useful for slowing the muscle loss (Sepulveda, et al. *Clin. Exp. Pharmacol. Physiol.* 2015). However, the disproportionate increase in the elderly population and the poor replicability of the results related to nutritional strategies, lead to consider skeletal muscle degeneration as a serious problem for human health and one of the main challenges faced by national health systems in industrialized countries.

Sphingolipids (SL) are essential molecules for maintaining the phenotype of a healthy skeletal muscle. SLs have been considered since long as stable structural components of the cell membrane; moreover, in the last decade, various studies have reported that they are also included in lipid rafts, i.e. in those molecular platforms that play a role in membrane signalling and trafficking, where the biologically active molecules move and are able to modulate processes biological (Maceyka M. et al. *Nature* 2014).

Among the bioactive sphingolipids, ceramide and Sphingosine 1-Phosphate (S1P) are mainly involved in controlling the cellular biology of the musculoskeletal system. Recently, the metabolic axis consisting of Sphingosine kinase (SphK) and S1P was included in the list of factors capable of modulating the musculoskeletal phenotype (Pierucci et al BBA *Mol Basis of Disease* 2018). Some physiological properties of the musculoskeletal tissue, such as muscle contractility, fatigue and adaptation are under the control of several bioactive sphingolipids, mainly ceramide and S1P, which act in opposite ways: ceramide inhibits strength and promotes fatigue, while S1P slows down fatigue, preserving strength over time (Danieli-Betto D, *Am J Physiol Cell Physiol.*, 2005). Moreover, S1P exerts a trophic action in isolated fibres in the excitation/contraction coupling, mainly mediated by S1P receptors (Sassoli C. et al., *J Cell Mol Med.*, 2011). Other studies carried out by the group of Danieli have highlighted the trophic role of S1P in a rat model of denervation atrophy, which significantly reduces adverse effects on muscle mass and on cross-sectional area after 1-2 weeks of tissue regeneration (Zanin M. et al., *Am. J. Physiol. Cell Physiol.*, 2008).

From the 1990s onwards, the sphingosine-1-phosphate receptors have been identified, named S1PR1, S1PR2, S1PR3, S1PR4 and S1PR5, the first three with an extensive gene expression in tissues, S1PR4 with prevalent expression in the immune system and S1PR5 with prevalent expression in the spleen, on Natural Killer (NK) cells, on other lymphocytes and in the central nervous system (CNS), mainly on oligodendrocytes (Chun et al., *Pharmacol. Rev.* 2010).

Several in vitro studies carried out on murine C2C12 cells (Yaffe and Saxel, *Nature*, 1977), models usually used to study the cellular and molecular biology of skeletal muscle precursors (cells and myotubes), underline the role of the S1P-mediated signalling pathway in the proliferation of myoblasts and in the process of myogenic differentiation. In C2C12 cells, S1P acts as a ligand of S1PR receptor subtypes, triggering several signalling pathways closely correlated with:

1) cell survival, through the activity of phospholipase D, of Protein Kinase C, of Akt etc. (Meacci E. et al., FEBS., 1999);
2) cellular cytoskeletal remodelling, through the transient and rapid association of RhoA and Rho kinase to the membrane, mobilization of $Ca^{2+}$ in an S1P2/S1P3 dependent manner (Meacci E. et al., FEBS Lett., 2000). Meacci E. et al., *Biochem. J.* 2002); and
3) the myogenic program, through the up-regulation of the expression of connexin-43, an intercellular junction membrane protein (Squecco R. et al., *Mol Biol Cell.*, 2006) and the up-regulation of some TRPC Channels, a class of cationic channels activated by the mechanical tension due to stretching of the musculoskeletal tissues (Meacci E, et al., *ell Mol Life Sci.*, 2010; Formigli L., Meacci E. *J Cell Physiol.* 2007).

In these studies, it was shown that changes in SphK functionality and S1PR expression occur in skeletal muscle tissue of cachectic animals (animals carrying the C26 tumour, a well-characterized experimental model of cancerous cachexia) and in C2C12 myotubes treated with dexamethasone, a system that mimics glucocorticoid-induced musculoskeletal atrophy. In particular, in both models of atrophy, the functional activity of SphK1 and the intracellular S1P are reduced, while the expression of the functional transporter S1P is upregulated. In particular, significant variations in the pattern of the S1PR1-5 subtype expressed in this cell line (S1PR1, S1PR2, S1PR3) occur in atrophic C2C12 myotubes and in skeletal muscle tissues obtained from cachectic mice, and more precisely an up-regulation of the S1PR2 expression and a down-regulation of S1PR1 and S1PR3.

The role of sphingolipid modulators in many cell types is well established, and in particular the role of S1P in regulating the response of muscle cells and of the musculoskeletal system, such as the signal cascade leading to cell survival, to cytoskeletal remodelling and to the correct balance between myogenic differentiation and myoblast proliferation. However, as far as the Applicant is aware, no molecule with a more or less high specificity towards S1PR receptors has been identified so far, that has found an actual utility in prophylactic or therapeutic treatments of atrophy.

On the other hand, however, the increase in the elderly population and in the pathologies associated with skeletal muscle degeneration, such as cancer or muscular dystrophy, makes particularly felt the need to identify as soon as possible molecules having a prophylactic and therapeutic efficacy towards atrophy or degeneration of skeletal muscles, or sarcopenia.

SUMMARY OF THE INVENTION

Now the inventors have surprisingly identified in a composition of molecules described in the following, a pharmaceutical composition useful for the prevention and the treatment of atrophy or degeneration of skeletal muscle, or of the sarcopenia.

In experimental studies on C2C12 cells, illustrated below in the experimental part of examples, the pharmaceutical composition of this invention has proved in particular to be efficacious in the prevention of the expression of atrogin/MAFbx induced by dexamethasone and by the Tumour Necrosis Factor alfa (or TNFα), and therefore it represents an efficient mean for the prophylaxis against atrophy or against the degeneration of skeletal muscle.

It is therefore a subject of this invention a pharmaceutical composition, whose essential characteristics are defined in the first of the attached claims.

A further subject of this invention is a pharmaceutical composition for use in the prevention and in the treatment of atrophy of skeletal muscle, whose essential characteristics are defined in the claim 7 here attached.

Further important features of the pharmaceutical composition and of the pharmaceutical composition for use in the prevention and in the treatment of atrophy of skeletal muscle according to the invention are defined in the dependent claims, also attached here, and illustrated in the following detailed description.

BRIEF DESCRIPTION OF THE DRAWINGS

FIGS. 3A, 3B, 3C (Comparison) show images of phase contrast microscope for C2C12 cells in the experiments described in the following Example 1, after treatment with Dexa and with the compounds or the combinations of compounds indicated.

FIGS. 4A and 4B (Comparison) show the representative result of the Western Blotting analysis and the graphs of the densitometric analysis of the expression of Atrogin-1/MAFbx in C2C12 myotubes by treatment with the compounds and the combinations of compounds indicated, as described in the following Example 1.

FIGS. 6A, 6 and 6C show the representative result of the Western Blotting analysis and the graphs of the densitometric analysis of the expression of Atrogin-1/MAFbx in C2C12 myotubes by treatment with a composition of the invention, as described in the following Example 2.

FIGS. 7A and 7B show images of phase contrast microscope of C2C12 cells in the experiments described in the following Example 2, after treatment with Dexa and with the combinations of the invention.

FIG. 8 shows the representative result of the Western Blotting analysis and the graph of the densitometric analysis of the expression of Atrogin-1/MAFbx in C2C12 myotubes by treatment with FTY720 and the composition of the invention and/or Dexa, as described in the following Example 2.

FIG. 12A shows the expression of Atrogin-1/MAFbx in C2C12 myotubes by treatment with a composition of the invention comprising CYM5478 as S1PR2 modulator, and/or with Dexa as described in the following Example 2.

DETAILED DESCRIPTION OF THE INVENTION

Figure 1:
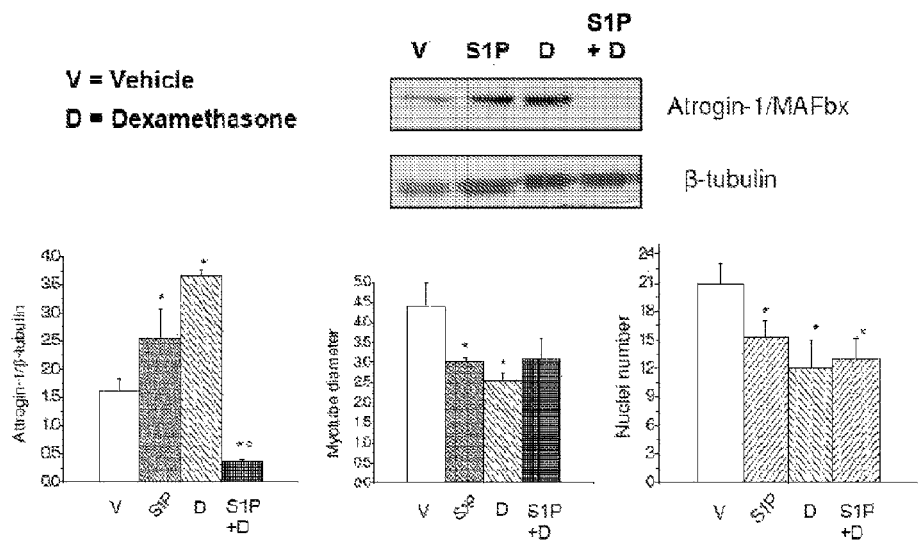
FIG. 1 (State of the Art) shows in the parts A, B and C respectively, the graph of the expression of Atrogin-1/MAFbx (FIG. 1A) and of the morphologic parameters of C2C12 myotubes (diameter and number of myonuclei) treated with a vehicle (dimethylsulphoxide or DMSO<0.05%) or with S1P before dexamethasone (indicated in this figure and in the following abbreviated sometimes as "Dexa") as described in the following experimental part.

The present pharmaceutical composition comprises a combination of the three components described in detail below, which are products available on the market, or of pharmaceutical acceptable salts thereof, and of at least a pharmaceutically acceptable excipients and/or carrier.

The first essential component of the present composition is a compound of formula (I)

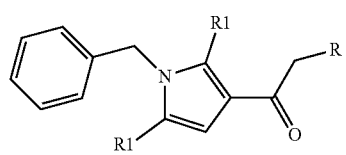
(I)

wherein
R is selected from the group consisting of chlorine, 6-oxo-1,6-dihydro-pyridine-3-carbonitrile

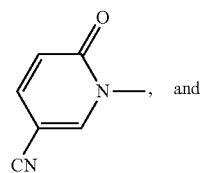

6-oxo-1,6-dihydro-piridin-3-trifluoromethyl

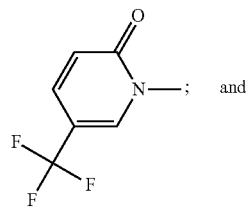

R1 is independently selected from the group consisting of H, (C1-C4)alkyl, phosphate and —$CH_2$-phosphate.

In a preferred embodiment of the invention, in the compound of formula (I) R1 is methyl.

According to a preferred embodiment of the present invention, in the compound of general formula (I) R is 6-oxo-1,6-dihydro-pyridine-3-carbonitrile, and R1 is methyl. This compound is also known as CYM5520 (CAS No. 1449747-00-5), a known agonist of the S1PR2 receptor, having high specificity, not showing any agonist activity towards the other receptors of S1P and never proposed so far for the development of drugs but just used as research tool for studying the mechanisms involving the S1PR2 receptor.

In a further embodiment of the invention, in the compound of general formula (I) R is chlorine and R1 is methyl. This compound is also known as EN300, and it is referred to as EN300 in the following too.

In a further embodiment of the invention, in the compound of general formula (I) R is 6-oxo-1,6-dihydro-pyridine-3-trifluoromethyl and R1 is methyl. This compound is also known as CYM5478 (CAS No. 870762-83-7), and it is so indicated in the following.

The second essential component of the pharmaceutical composition of the invention is the (3R)-3-amino-4-[(3-hexylphenyl)amino]-4-oxobutyl]-phosphonic acid also known with the code W 146 (CAS No. 909725-61-7), known as having an antagonist activity towards the S1PR1 receptor. As far as the Applicant is aware of, this compound has been never proposed so far as active principle against atrophy or against degeneration of skeletal muscle or sarcopenia, either alone or in combination with other compounds having a modulating activity of the S1PR receptors.

The third essential component of the pharmaceutical composition of the invention is selected amongst the following compounds:

[2-amino-2-(3-octyl-phenylcarbamoyl)-ethyl] ester of phosphoric acid, CAS No. 449173-19-7, also known as VPC 23019, known to be an antagonist of S1PR1 and of S1PR3, but never proposed so far as active principle against atrophy or degeneration of skeletal muscle or of sarcopenia, either alone or in combination with other compounds having a modulating activity of S1PR;

2-(4-chlorophenyl)hydrazide of N-(4-chlorophenyl)-3,3-dimethyl-2-oxobutaneimidic add, CAS No. 934369-

14-9, also known as TY52156, and so indicated in the following too, known as being an antagonist of the S1PR3 receptor: and a molecule siRNA (short interfering RNA) having sequence SEQ ID NO:1, which is a molecule of double-stranded RNA of 21 nucleotides corresponding to a region of the gene capable of silencing the expression of the S1PR3 receptor leading to a reduction of expression of about 40%.

Each of the three essential components of the present pharmaceutical composition, as described above, can be moreover replaced by a pharmaceutically acceptable salt thereof, for example W146 can be replaced by the corresponding trifluoroacetate salt thereof.

According to a particular embodiment of the invention, the present composition is administered at a concentration for each of the three components described above ranging between about 0.1 µM and about 5 µM. Preferably, the present composition comprises compound of formula (I) and W146 in the same concentration, to which a concentration is added of VPC23019, TY52156 or si-RNA of SEQ ID NO:1 equal to about half the concentration of the other two components. Particularly efficacious is the present composition comprising compound of formula (I), preferably CYM5520, VPC23019 and W146 in the following concentrations: 2 µM CYM5520+1 µM VPC23019+2 µM W146.

In an embodiment of this invention, the present pharmaceutical composition can moreover comprise one or more other active principles, such as fingolimod.

In the present invention by the term "pharmaceutically acceptable" is meant a product that is biologically free from side effects, i.e. it does not cause an unacceptable amount of side effects or of deleterious interactions with a biological system, such as a human or animal, to which the product is administered.

By the term "excipient" is meant herein any excipient or adjuvant commonly used in the formulation of pharmaceutical active principles, which can be easily chosen by a skilled person depending on the nature of the active principle, of the administration route and of the type of desired formulation. Examples of excipients include, without being limited to, colorants, flavourings, preservatives, wetting agents, fillers, emulsifying and dispersing agents, agents for modifying release of the active principle, such as coating agents for oral formulations.

By the term "carrier" is meant herein any agent able to assist formulating, carrying and releasing of the active principle in the pharmaceutical composition; it includes, without being limited to, solvents, diluents and vehicles.

As shown in the following examples, the present pharmaceutical composition has proved to be surprisingly efficacious in inhibiting the onset of atrophy or the degeneration of skeletal muscle, caused by pathologies or due to aging (sarcopenia). The more common causes of atrophy include, without being limited to, aging, prolonged immobilization, heart failure, cancer, chronic lung failure and chronic renal failure, and glucocorticoid- and cytokine-dependent diseases.

The following examples are provided for illustrative, non-limitative, purposes of the present invention.

EXAMPLES

Materials Used

Dulbecco's Modified Eagle's Medium (DMEM), foetal calf serum (FCS), penicillin/streptomycin, and the inhibitory cocktail of protease and bovine serum albumin were all purchased from Sigma (Milan, Italy). The C2C12 cells were obtained from the American Type Culture Collection (ATCC, Manassa, VA, USA). Dexamethasone (Dexa) and CYM5520 were purchased from Sigma (Milan, Italy). Sphingosine 1-phosphate (S1P), VPC23019, FTY720 and W146 were from Tocris (Bristol, UK). The TRIzol, the High Capacity cDNA Reverse Transcription kit, and the Syber Green reagent were from Life Technologies, Thermo Fisher Scientific, (Carlsbad, CA, USA); the Bradford assay (microassay) for measuring the protein concentration and the non-fat dry milk in blocking buffer came from Bio-Rad, (Hercules, CA); Amersham Hybond p0.45 PVDF membrane and the chemiluminescence kit were from GE Healthcare (Buckinghamshire, UK); the anti-Atrogin-1/MAFbx polyclonal rabbit antibody came from ECM Biosciences (Versailles, KY, USA); the anti-β-actin antibodies and the secondary antibodies conjugated with horse radish peroxidase came from Santa Cruz Biotechnology (Santa Cruz, CA, USA).

Methods Used

Cell Cultures and Treatments

C2C12 murine skeletal myoblasts obtained from the American Type Culture Collection (ATCC, Manassas, VA, USA) were cultured in Dulbecco's Modified Eagle's Medium (DMEM) (Sigma, Milan, Italy) with L-glutamine 1%, penicillin/streptomycin 1% (Sigma, Milan, Italy) and Foetal Bovine Serum 10% (FBS) (Sigma, Milan, Italy). For experiments with the myotubes, myoblasts were seeded in 6-wells plates at a concentration of $0.2 \times 10^6$ cells/ml. When the cells reached 90-100% confluence (72 hours after seeding), the medium was replaced with the differentiation medium (DM), consisting of DMEM containing antibiotics, glutamine and horse serum (HS) 2% (Sigma, Milan, Italy). The medium was changed every 24-48 hours. The complete cell differentiation was observed after 4-6 days of incubation with HS 2%. The C2C12 skeletal myotubes were incubated for 24-48 hours with the indicated compounds: Sphingosine 1-phosphate (S1P) 2 µM, or different concentration of CYM5520, VPC23019 and/or W146 (in the concentration range between 0.25 and 2 µM). CYM5478, TY52156 and siRNA specific for S1PR3 (NCBI ref NM_010101.4, sequence 5'-CGGGGUCCUCUGCAAGUGA-3 '1118-1139 SEQ ID NO: 1, same size random oligonucleotides were used as negative control SCR-siRNA) were used in some of the experiments. The agonists/antagonists or S1PR3-siRNA or SCR-siRNA were added to the culture medium for 1 hour prior to treatment of the myotubes with dexamethasone (Dexa) 100 µM for 48 hours.

Microscopic Observation of the Cellular Morphology

After the various treatments at 24/48 hours the cultures were observed under the phase contrast microscope (NIKON). The images shown are representative of n. 5-6 observation frames for each treatment.

Western Blot Analysis

The Western Blotting analysis was carried out for determining the protein levels of Atrogin-1/MAFbx in C2C12 myotubes. The cells were lysed at 4° C. with RIPA buffer containing TrisHCl 50 mM, pH 7.5, NaCl 120 mM, EDTA 1 mM, EGTA 6 mM, $Na_4P_2O_7$ 15 mM, NaF 20 mM, 1% of cocktail Nonidet and protease inhibitor (1.04 mM AEBSF, 0.08 mM of aprotinin, leupeptin 0.02 mM, bestatin 0.04 mM, pepstatin A 15 mM, E-64 14 mM (Sigma, St. Louis, MO, USA). The lysates were centrifuged at 600×g for 6 min at 4° C., and the proteins concentration was measured by using the Bradford assay (Bio-Rad, Hercules, CA). Aliquots containing 40 µg of proteins were diluted in loading buffer 2× (10% SDS, 50% glycerol, 0.25% bromophenol blue and 0.25 M Tris-HCl, pH 6.8) and boiled at 90° C. for 10 minutes to denature proteins. The samples were subjected to SDS-polyacrylamide 10-12% (SDS-PAGE) gel electrophoresis and to Western blotting on Amersham Hybond p 0.45 PVDF membrane (GE Healthcare, Buckinghamshire, UK). The membranes, after sufficient washings with phosphate buffer saline PBS have been initially blocked with PBST buffer (150 mM NaCl, 0.05% Tween-20 and 20 mM Tris-HCl, pH 7.4) containing 5% of non-fat dry milk (Bio-Rad, Hercules, CA) for 1 hour at room temperature. After blocking, the membranes were washed in PBST and then incubated overnight with a 1:1000 dilution of the primary antibody comprising rabbit polyclonal antibody with Atrogin-1/MAFbx. After sufficient washings with PBST, the membranes were incubated for 1 hour at room temperature with secondary antibodies conjugated with goat anti-rabbit or goat anti-mouse horseradish peroxidase (Santa Cruz, Texas, USA) at dilution 1:10.000/1:5.000. Following three washings with PBST, the bands corresponding to the immunoreactive proteins were seen by using reagents for the detection of the Western blotting ECL (GE Healthcare, Buckinghamshire, UK); and finally, the membranes were exposed to a high performance chemiluminescence film (GE Healthcare, Buckinghamshire, UK). The identity of the bands on the Western Blot membranes was confirmed by comparing them with a high-precision marker having a known molecular weight (BioRad, Hercules, CA). Densitometric analysis of the bands was performed by using NIH IMAGE J (ImageJ software, Bethesda, MD, USA) and Quantity-One (imaging and analysis software from Bio-Rad Laboratories, Hercules, CA) and the intensity of the band was indicated as a relative percentage (mean and standard deviation from the mean), obtained by calculating the ratio of the specific protein with respect to the β-actin intensity and normalizing it to the control, set to 1.

Quantification of mRNA and of the Expression by Quantitative Real-Time Polymerase Chain Reaction (qPCR)

The levels of mRNA of Atrogin-1/MAFbx were quantified by real time PCR. Primers specific for Atrogin-1/MAFbx and gene GAPDH (Glyceraldehyde-3-Phosphate Dehydrogenase) were designed by using the software NCBI BLAST NUCLEOTIDE (Rockville Pike, Bethesda MD, USA). The mRNA of GAPDH was the endogenous control used for normalization of the concentrations of mRNA of the target gene. The total RNA was extracted by using the reagent TRIzol (Invitrogen, Carlsbad, CA, USA). The amount and quality of the RNA extracts were measured by using a Nanodrop (Thermo Scientific, Waltham, Massachusetts, USA). The cDNA of the first filament was synthesised in a reaction of reverse transcription (RT) in a volume of 20 µl with 0.5 µg of RNA using a high-capacity cDNA reverse transcription kit (Life Technologies, Carlsbad, CA, USA). The reaction conditions were selected as follows: for 10 minutes at 25° C., 120 minutes at 37° C., 5 minutes at 85° C. and subsequently the samples were stored at −20° C. The real time PCR reaction was carried out in a volume of 25 µL and consisted in cDNA 100 ng, 0.25 µM of each primer and Power SYBR Green PCR Master Mix (Life Technologies, Carlsbad, CA, USA).

The gene amplification was carried out in a PCR Fast Real-Time system 7500 (Applied Biosystems, CA, USA) based on these thermal conditions: 95° C. for 10 minutes, followed by 40 cycles at 95° C. for 30 seconds, 53-55° C. for 30 s, 72° C. for 45 s (fluorescence was acquired during the elongation stage), finally followed by 95° C. for 15 s, 60° C. for 60 s, 95° C. for 15 s and 60° C. for 15 s for the dissociation analysis. The sequences of the forward and reverse primer are listed here:

```
Atrogin-1/MAFbx:
Forward
                                  (SEQ ID NO: 2)
5'-GCAGCCAAGAAGAGAAAGAA-3', Reverse
                                  (SEQ ID NO: 3)
5'-CTGTGACTTTGCTATCAGC-3'
and GAPDH:
Forward
                                  (SEQ ID NO: 4)
5'-GGCAAATTCAACGGCACAGTC-3', Reverse
                                  (SEQ ID NO: 5)
5' TCGCTCCTGGAAGATGGTG-3';
``` in each test were included both positive and negative controls. The relative transcription levels were calculated based on the formulae: fold=$2^{-\Delta\Delta Ct}$ wherein $\Delta Ct$ is the difference of Ct between the target gene and the housekeeping gene (constitutive and control gene), and $\Delta\Delta Ct$ is the difference between $\Delta Ct$ of the sample of interest and the reference $\Delta Ct$. The levels of messenger RNA in the control were arbitrarily set at 1.0.

Statistical Analysis

Data in the following examples were reported as mean±SEM of at least 3 independent experiments. The statistical significance was determined by a multiple comparison test one-way ANOVA or by the Student t-test. A value $p<0.05$ was considered as statistically significant. Calculations were done by using GraphPad INSTAT. Densitometric analysis was carried out by using the software Image J, Bethesda, MD, USA.

Involvement of the S1P-Mediated Signalling in the Acquisition of the Atrophy Phenotype in C2C12 Myotubes To analyse the role of S1PR-related skeletal muscle atrophy, we used C2C12 myotubes exposed to the glucocorticoid (GC), dexamethasone (Dexa). This experimental model was chosen for the following reasons: 1) several studies have reported that the administration of GC to healthy animals or myocyte cultures results in the activation of common pathways of intracellular signalling that ultimately generate a hypercatabolic drive comparable to that occurring in the cancerous cachexia; 2) the GC levels are often over-regulated in cachexia in both the experimental and human models; 3) the GCs are widely used in chemotherapy regimens, possibly contributing to cancer- and chemotherapy-induced cachexia; 4) we recently reported that sphingolipid signalling and S1PR expression pattern are very similar in GC-treated C2C12 myotubes and in the skeletal muscle tissue from animals carrying the C26 tumour, a well-characterized experimental model of cancerous cachexia (Pierucci et al., *BBA Mol Basis of Disease* 2018). In the literature studies are reported on muscular atrophy induced by the incubation of myotubes with the Tumour Necrosis Factor alfa (TNFα) (De Larichaudy et al., 2012 Skeletal Muscle).

To test the role of exogenous S1Ps, the terminally differentiated myotubes were treated with the bioactive lipid. In particular, the C2C12 myoblasts were allowed to grow and come to confluence, then allowed to differentiate in the medium for 4 days. Differentiated myotubes were treated with the control (Vehicle Treated) or S1P (1 µM) before dexamethasone (Dexa, 100 µM) for 48 hours. Cell lysates (40 µg) were subjected to SDS-PAGE and immunoblotting with specific anti-Atrogin-1/MAFbx antibodies, marker of muscular atrophy. A representative blot of three independent experiments and the densitometric analysis of Atrogin-1/MAFbx in untreated myotubes and in myotubes treated with Dexa, is shown. The data (mean±SEM) normalized to the β-tubulin band are shown in the graph as a percentage with respect to the control (Student t-test, *$p<0.05$ vs control; $p<0.05$ vs Dexa). (from Pierucci F, Frati A, Battistini C, Matteini F, Iachini M C, Vestri A, Penna F, Costelli P, Meacci E. *Biochim Biophys Acta Mol Basis Dis.* 2018 December; 1864(12): 3598-3614.

Results in FIG. 1 show that S1P is able to significantly increase the expression of Atrogin-1/MAFbx (FIG. 1A) and to slightly change the morphological parameters of the myotubes (diameter and number of myonuclei) (FIG. 1B e 1C). Conversely, the addition of S1P to the myotubes before incubation with the glucocorticoid Dexamethasone (Dexa) is able to reduce the Atrogin-1/MAFbx level, restoring the basal levels by counteracting the effect of Dexa. However, no significant changes in cell morphology and in the number of nuclei were observed in Dexa-treated cells in the presence of S1P. This apparent contradiction may be explained by the different action of S1P-triggered signalling in Dexa-treated myotubes versus untreated cells, due to the difference in the expression pattern of S1PR subtypes. Indeed, in the skeletal muscle tissue of the C26 hosts compared to healthy mice and in myotubes treated with Dexa compared to untreated cells, the expression of S1PR1 and S1PR3 is decreased, while the expression of S1PR2 is increased (Pierucci et al., 2018). This suggests a potential role for signalling pathways downstream of S1PR subtypes in controlling cell atrophy.

Example 1—Comparison

Involvement of S1PR2 in Expression of the Atrophy Marker in C2C12 Myotubes

The onset of musculoskeletal tissue atrophy depends on the expression of specific transcriptional factors that lead to the expression of Atrogin-1/MAFbx. Therefore, to study the downstream signalling pathways of each specific S1PR subtype, the expression level of the atrophic marker in C2C12 myotubes was evaluated using specific S1PR agonists and/or antagonists. Previous data reported in Pierucci et al. (BBA Mol Basis of Disease 2018) indicate that S1PR2 is increased in Dexa-treated cells suggesting that activation of the S1P2-downstream signalling pathway may be required for cell atrophy.

The C2C12 myoblasts were let to grow on a coverslip and to reach confluence, then they were moved onto a differentiated medium for 4 days. A cell lysate (40 µg) obtained from C2C12 myotubes treated with the vehicle (DMSO at final concentration lower than 0.1%) or with the single S1PR modulator (2 µM of CYM5520 or 1 µM VPC23019 or 2 µM W146) before the vehicle or dexamethasone (100 µM, Dexa) for 48 hours, was subjected to SDS-PAGE and immunoblotting with specific anti-Atrogin-1/MAFbx or β-actin antibodies. A representative blot of at least three independent experiments and densitometric analysis was shown. The data (mean±SEM) normalized to the β-actin band are reported in the histograms as percentage relative to the control set as 1 (one-way ANOVA, *$p<0.05$ vs control; \$ $p<0.05$ vs Dexa; § $p<0.05$ vs modulator alone).

Figure 2A:
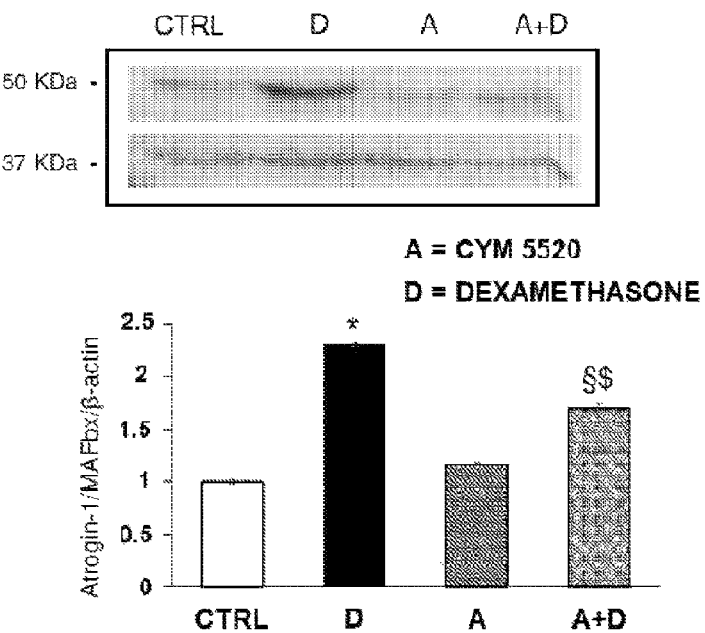
FIG. 2 (Comparison) shows in the parts A, B, C, D, the representative result of the Western Blotting analysis, the graphs of the densitometric analysis of the expression of Atrogin-1/MAFbx in C2C12 myotubes by treatment with the compounds indicated, as described in the following Example 1.

Surprisingly, as shown in FIG. 2A, when the C2C12 myotubes were treated with CYM5520 alone, a specific agonist of S1PR2 in absence of Dexa, no increase was observed in the amount of Atrogin-1/MAFbx and incubation with CYM5520 before Dexa has only slightly counteracted the GC effect remains the level of atrophic markers significantly higher than in the control.

Subsequently, as the expression of S1PR1 and of S1PR3 appeared decreased in myotubes treated with Dexa, the cells were incubated in the presence of an antagonist of S1P1 and S1P3, using alternatively VPC230189 or W146, each alone. As shown in FIGS. 2B and 2C, treatment with VPC28019 or W146 each alone did not induce the expression of Atrogin-1/MAFbx. Also, when both antagonists were used alone before the GC, they did not counteract the effect of Dexa.

Overall, these data suggest that although the expression level of S1PR2 increased and S1PR1 and S1PR3 decreased after treatment with Dexa, the downstream signalling of each S1PR alone in the presence of GC does not interfere with the expression of Atrogin-1/MAFbx, probably indicating the existence of a functional crosstalk between different S1PR subtypes.

The effect of administering the single active S1PR modulator was also compared with the effect of FTY720/Fingolimod, a small molecule acting as an agonist of S1PR. This agent has received approval as a drug for the treatment of multiple sclerosis (Gilenya, Novartis) (Chun et al., *Pharmacol. Rev.* 2010) from the Food and Drug Administration and the European Medicines Agency. When phosphorylated by SphK2 in vivo (Brinkmann et al., *Nat Rev Drug Discov.* 2010), phospho-FTY720 is structurally analogous to S1P and binds and activates S1PR1-3-4-5, but not S1PR2. In particular, the long-term activation of S1PR1 by FTY720-P determines the internalization and degradation of the receptor, thus acting as an S1PR1 antagonist (Gonzalez-Cabrera et al., *Mol Pharmacol.* 2012).

As shown in FIG. 2D, Dexa-induced upregulation of Atrogin-1/MAFbx expression was not affected by the incubation of FTY720. In particular, this is the first evidence that FTY720 does not affect GC-induced myotube atrophy.

Figure 3A:
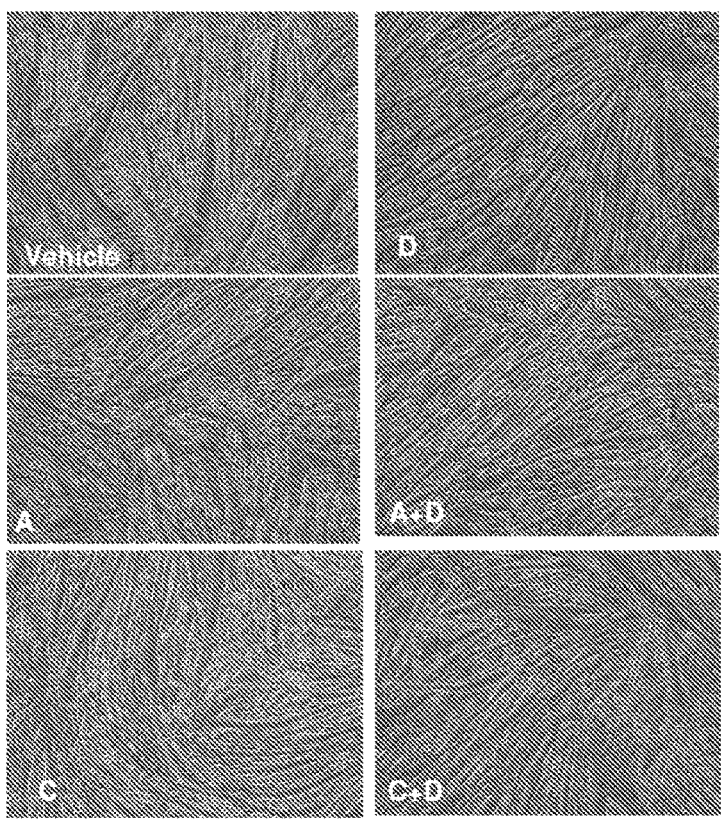
Figure 3B:
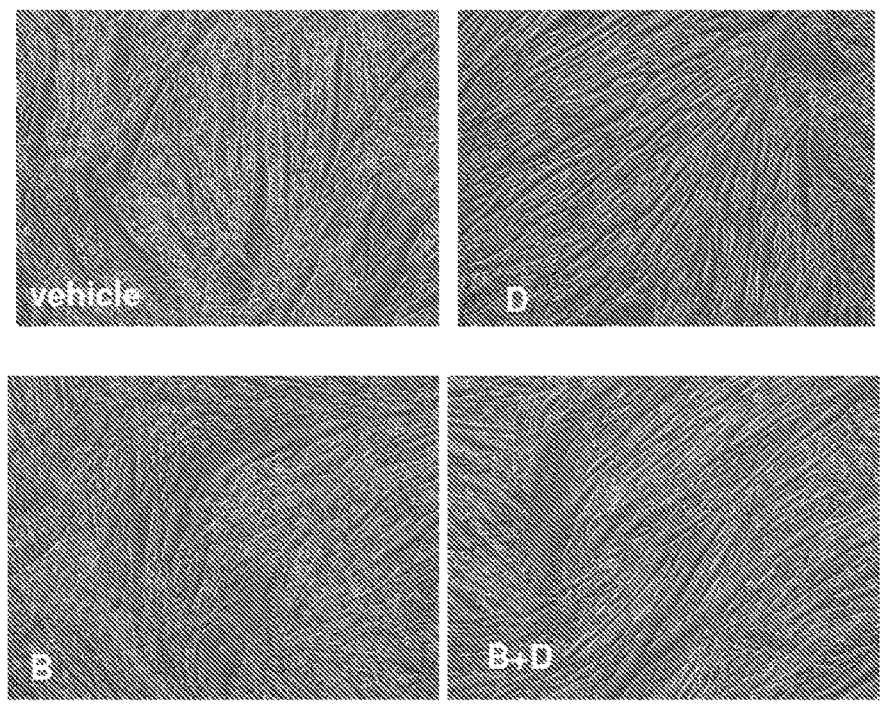

Effect of the S1PR Modulators in the Acquisition of Atrophic Phenotype in C2C12 Myotubes The above reported data have been confirmed by the analysis of the cellular morphology and of the quantification of the myotubes diameter and of the number of myonuclei. The C2C12 myoblasts were let to grow on a coverslip and when confluent they were moved on a differentiated medium for 4 days. The myotubes were then treated with the control or with a single S1PR modulator (2 µM CYM5520 or 1 µM VPC23019 or 2 µM W146 and/or dexamethasone (Dexa) for 48 hours, the cells were fixed and observed under microscope. The images in FIGS. 3A, 3B and 3C are representative of 3 experiments with similar results. The differentiated cells (control) show a big body and 3-8 myonuclei because of the fusion of the single cells during the myogenesis process. To be noted is the reduced diameter of the myotube and the number of myonuclei in the cells treated with the atrophy inducer Dexa with respect to the control and the effect of the indicated treatment on these parameters with respect to control and Dexa.

As shown in the Figures from 3A to 3C, the treatment with Dexa alone involved a reduction of the cells size and the reduction in the number of multiple myonuclei. These events were not significantly reduced when the treatment with GC followed the incubation with the S1PR modulator (CYM5520 or W146 or VPC23019), indicating that none of the three compounds alone has significantly affect the cellular atrophic morphology.

On the other hand, the morphological analysis indicated that the treatment with FTY720 was able to promote the formation of small autophagic vesicles (FIG. 3C).

Involvement of Combined S1PR Modulators in the Regulation of the Expression of Atrogin-1/MAFbx and Acquisition of the Atrophic Phenotype in C2C12 Myotubes The C2C12 myotubes were treated with a combination of two S1PR modulators selected from among CYM 5520, W146 and VPC23019. Cell lysates (40 µg) obtained from C2C12 myotubes treated with the vehicle (DMSO at concentration lower than 0.05%) or with the combination of two S1PR modulators (2 µM CYM5520 and/or 1 µM VPC23019 and/or 2 µM W146 before the control (vehicle DMSO less than 0.1% of final concentration) or dexamethasone (100 µM) (D, Dexa) for 48 hours. The proteins detection was carried out as in FIG. 4 by Western Blotting analysis. The data (mean±SEM) normalized to the β-actin band are reported in the graph as percentage with respect to the control set as 1 (one-way ANOVA, *p<0.05 vs control; § p<0.05 with respect to the modulator alone).

As it can be observed in FIGS. 4A and 4B, neither the combination of CYM5520 and VPC23019, nor the combination of VPC23019 and W146, nor the combination of CYM5520 and W146 were able to abolish the effect of Dexa in promoting the expression of Atrogin-1/MAFbx. Moreover, only the combination of VPC23019 and W146 has slightly induced the expression of atrophic marker while the combination of CYM5520 and VPC23019 and the combination of CYM5520 and W146 have had no significant effect.

These data suggest that the inhibition of S1PR3 and S1PR1 can be by itself a condition that favours cellular atrophy and under physiological conditions the expression of these two S1PR subtypes is crucial for the maintenance of the normal differentiated phenotype.

Figure 5A:
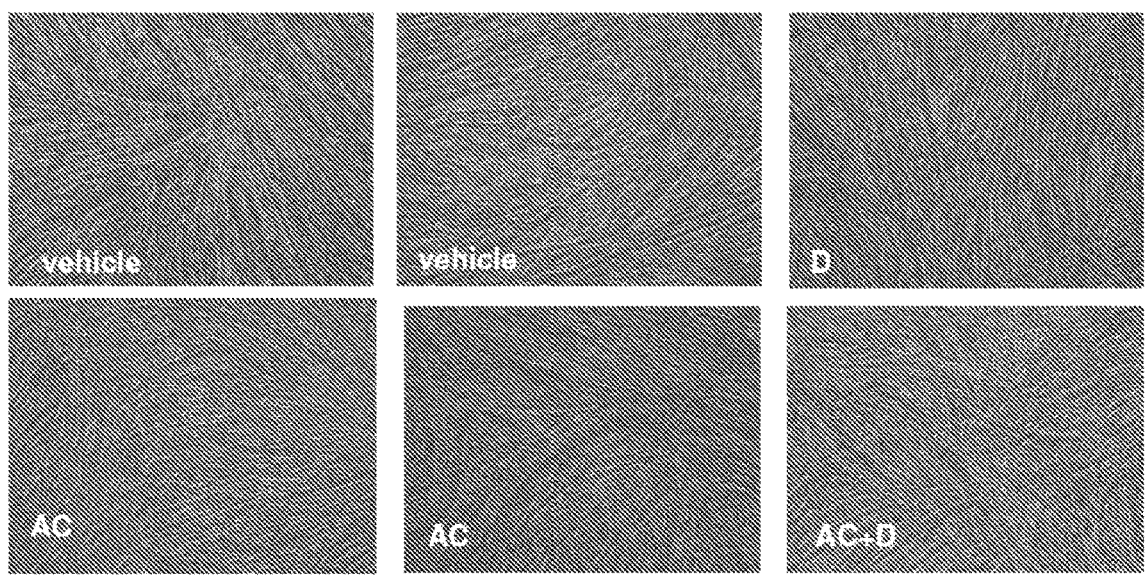
FIGS. 5A, 5B, 5C (Comparison) show images of the phase contrast microscope of C2C12 cells in the experiments described in the following Example 1, after treatment with Dexa and with the compounds or the combinations of compounds indicated.
Figure 5B:
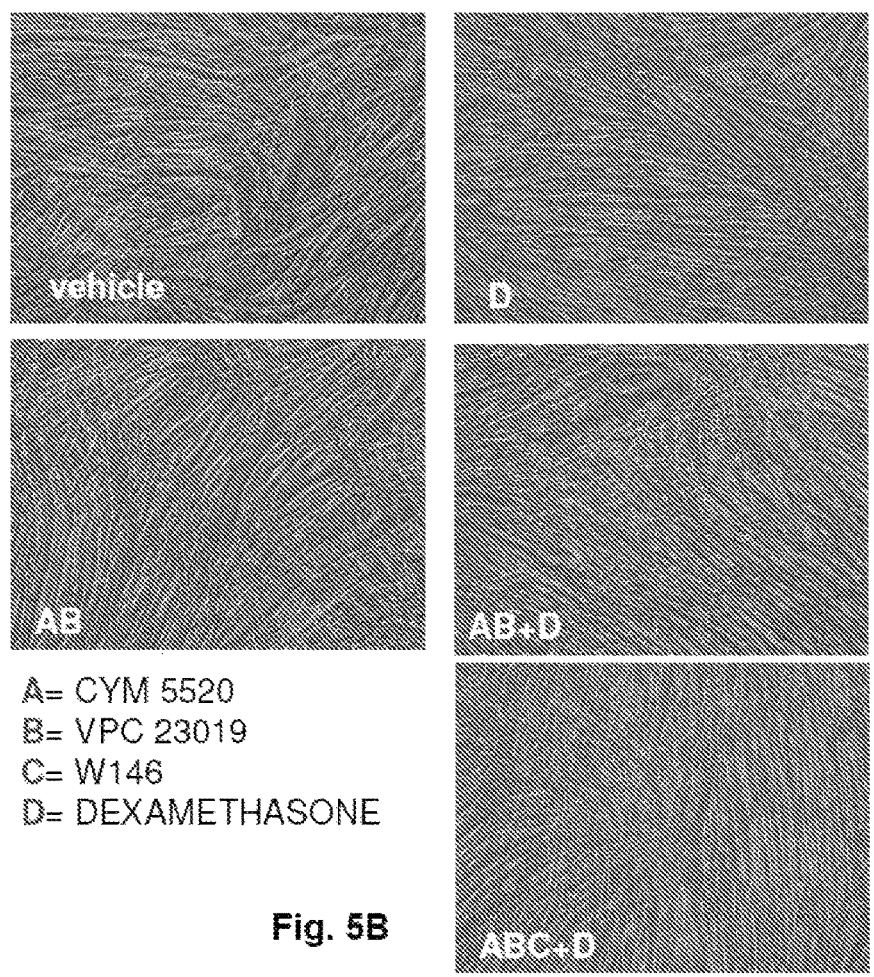
Figure 5C:
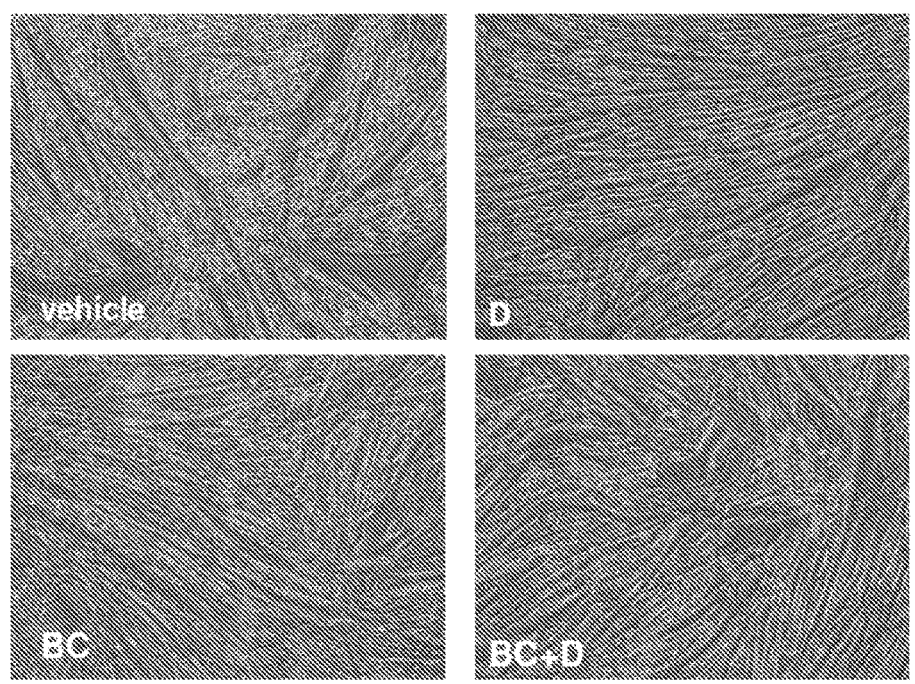

The analysis of the cellular morphology reported in FIGS. 5A, 5B and 5C confirms the trophic function of the signalling pathway downstream of S1PR1 and S1PR3. Cells treated as described above were observed under phase contrast microscope. The images are representative of three independent experiments with similar results. To be noted is the reduced diameter of the myotubes and the number of myonuclei in the cell treated with atrophic inducer Dexa with respect to the control and the effect of the indicated treatment on these parameters with respect to the control and Dexa.

Example 2

Involvement of the Composition of the Invention in the Regulation of the Expression of Atrogin-1/MAFbx and in the Acquisition of the Atrophic Phenotype in the C2C12 Myotubes The C2C12 myotubes were treated with the composition of the invention containing the three modulators CYM5520, VPC23019 and W146. Cell lysates (40 µg) obtained from C2C12 myotubes treated with a vehicle (DMSO at concentration <0.05%) or with the combination of two/three S1PR modulators (2 µM CYM5520 and/or 1 µM VPC23019 and/or 2 µM W146 before the control (DMSO lower than 0.1% final concentration) or dexamethasone (100 µM) (D, Dexa) for 48 hours have been analysed. The detection of the proteins was carried out as in FIG. 6 by Western Blotting analysis. The data (mean±SEM) normalized to the β-actin band are reported in the graph as percentage with respect to the control set as 1 (one-way ANOVA, *p<0.05 vs control; $ p<0.05 vs Dexa; § p<0.05 vs three modulators or two modulators combined).

Figure 6A:
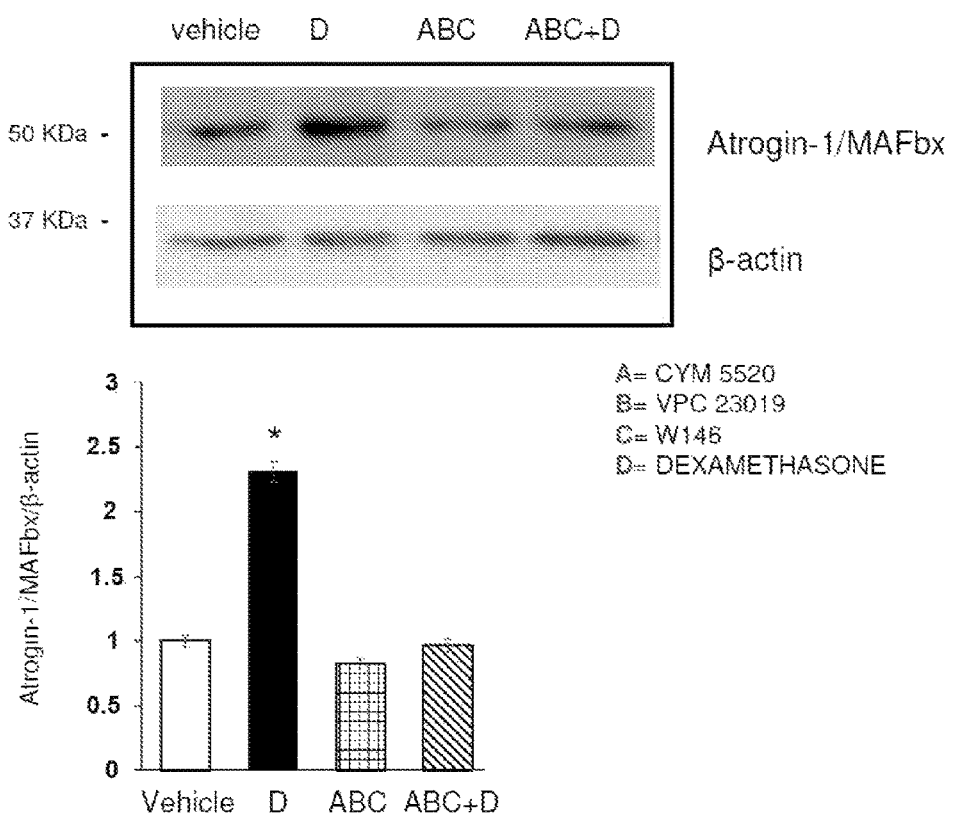
Figures 6B, 6C:
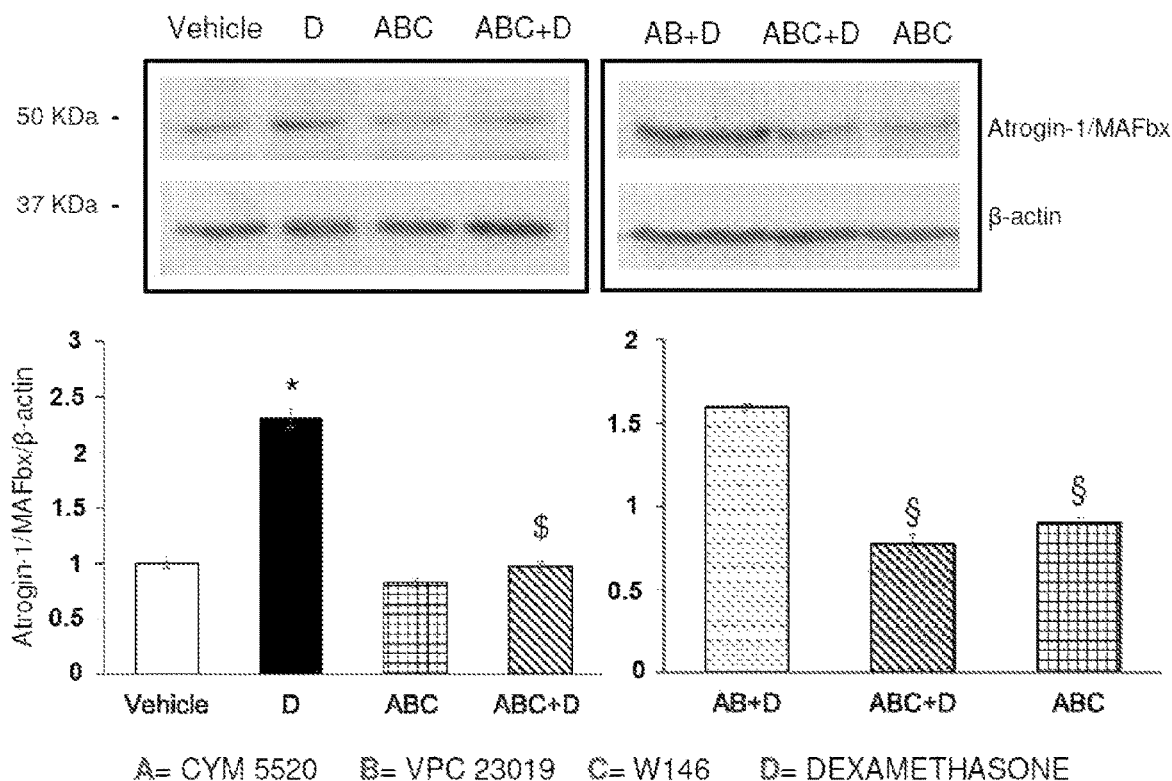

As reported in the FIGS. 6, the treatment with the three S1PR modulators together, 1 hour before the treatment with Dexa, has completely prevented the effect of GC on the expression of Atrogin-1/MAFbx, and in a different way with respect to what observed when the single compound was used alone (e.g. VPC23019), the three modulators combined appeared without any effects if used in the absence of Dexa.

Figure 7A:
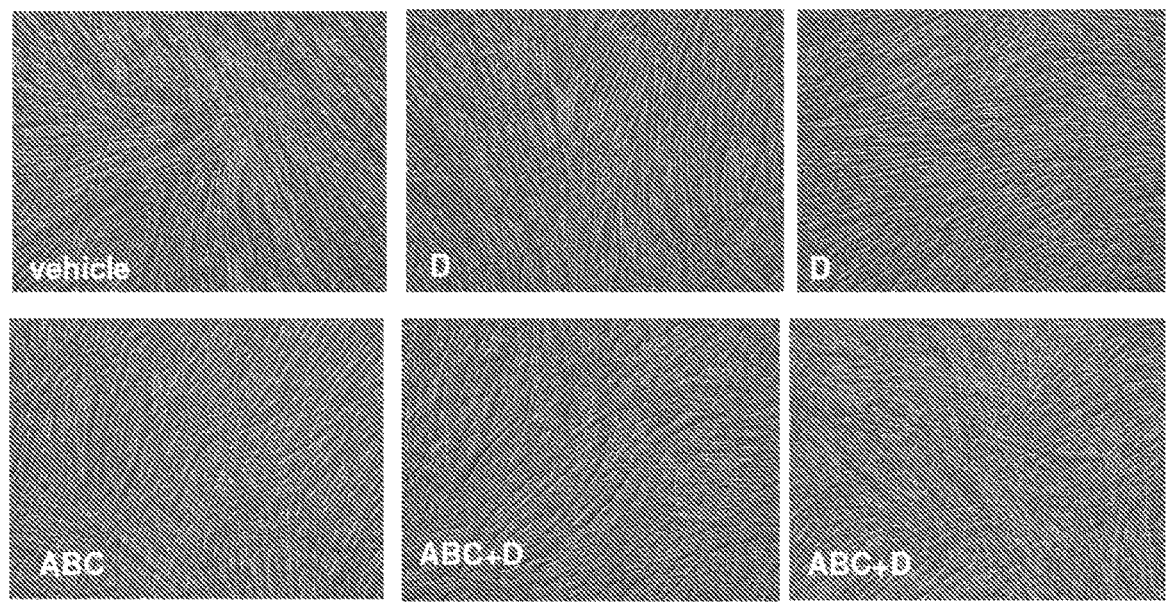

The morphological analysis of the treated myotubes confirmed the ability of the composition subject of this invention to prevent the onset of an atrophic phenotype after 48 hours of treatment with Dexa (FIG. 7A). The images in FIG. 7 are representative of three separated experiments with similar results. To be noted is the reduced diameter of the myotubes and the number of myonuclei in the cell treated with the atrophic inducer Dexa vs control, and the effect of the treatment with the composition of the invention on these parameters with respect to control and Dexa.

The administration of the S1PR modulators to the myotubes 24 hours after the treatment with Dexa resulted in no significant effect on the morphological parameters (FIG. 7B), indicating the relevance of the incubation of the cells with the composition 1 hour before Dexa or at least at the same time of the GC (data not shown), thus suggesting the importance of a modulation action before atrophy inducer (Dexa).

Cell lysates (40 µg) obtained from C2C12 myotubes treated with control (vehicle DMSO) or with FTY720 (2 µM) and with the combination of the three S1PR modulators (2 µM CYM5520 and 1 µM VPC23019 and 2 µM W146) before the vehicle DMSO (lower than 0.1% final concentration) or dexamethasone (100 µM) (D, Dexa) for 48 hours were analysed. The proteins detection was carried out as in FIG. 3 by Western Blotting analysis. The data (mean±SEM) normalized to the β-actin band are reported in the graph of FIG. 8 as percentage with respect to the vehicle set as 1 (one-way ANOVA, * p<0.05 vs control; $ p<0.05 vs Dexa; § p<0.05 vs the three modulators combined).

Figure 9:
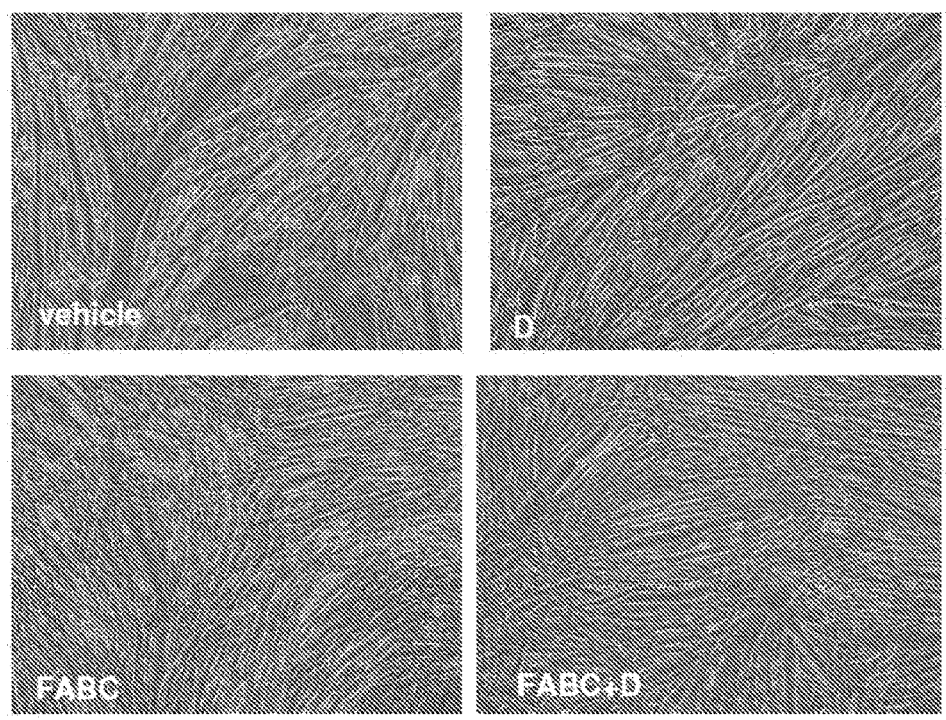
FIG. 9 shows images of phase contrast microscope of C2C12 cells in experiments described in the following Example 2, after treatment with Dexa, FTY720 and with the combinations of the invention.

The C2C12 myotubes were grown on Petri plates and when confluent were moved onto a medium for differentiation for 4 days. Cells were treated with control (Vehicle Treated) or with FTY720 (2 µM) and with the combination of the three S1PR modulators (2 µM CYM5520 and 1 µM VPC23019 and 2 µM W146) with first the vehicle DMSO (less than 0.1% of final concentration) or dexamethasone (100 µM) (Dexa) for 48 hours. Then, the cells have been observed with a microscope. Images in FIG. 9 are representative of three separated experiments with similar results. To be noted is the reduced diameter of the myotubes and the number of myonuclei in the cells treated with the combination of FTY720 together with the combination of the three S1PR modulators versus the control and Dexa.

Effect of the Different Concentration of the Three Modulators in the Present Composition and/or Dexamethasone on the Cellular Morphology of the C2C12 Myotubes The three S1PR modulators in the composition of the invention have been combined at different concentrations/stoichiometry, as follows:

Combination A-ATROFI (2 µM CYM5520+1 µM VPC23019+2 µM W146),
Combination MIX-I (1 µM CYM5520+1 µM VPC23019+1 µM W146),
Combination MIX-II (1 µM CYM5520+0.5 µM VPC23019+1 µM W146),
Combination MIX-III (0.5 µM CYM5520+0.5 µM VPC23019+0.5 µM W146),
Combination MIX-IV (0.5 µM CYM5520+0.25 µM VPC23019+0.5 µM W146),
Combination MIX-V (0.1 µM CYM5520+0.05 µM VPC23019+0.1 µM W146), Combination MIX-VI (2 μM CYM5520+1 μM VPC23019+1 μM W146),
Combination MIX-VII (3 μM CYM5520+2 μM VPC23019+3 μM W146),
Combination MIX-VIII (5 μM CYM5520+4 μM VPC23019+5 μM W146), The cell lysates (40 μg) obtained from C2C12 myotubes treated with the vehicle or with the combination of the three mixtures S1PR, 1 hour before the treatment with dexamethasone (100 μM) (D, Dexa) for 48 hours, were analysed. The data (mean±SEM) normalized to the β-actin band are reported in the graph as percentage related to the effect of the A-ATROFI combination set on 1 (Student t-test, *p<0.05 vs Dexa and other treatments). As it can be observed in the FIGS. 10, the maximum effect in the prevention of the expression of Atrogin-1/MAFbx induced by Dexa and in the morphological changes was obtained by using the combination A-ATROFI of the invention here described.

Figure 10A:
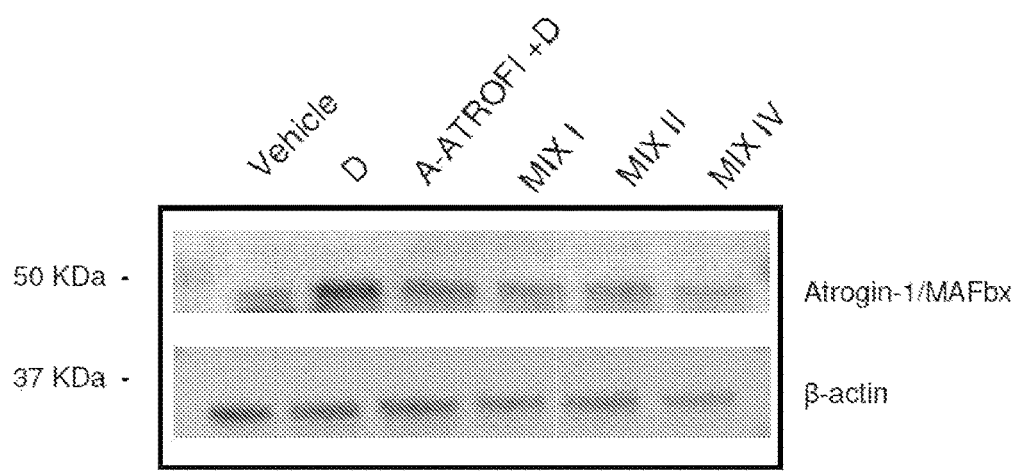
FIGS. 10A, 10B and 10C show the Western Blotting result and the graphs of the densitometric analysis for the expression of Atrogin-1/MAFbx in C2C12 myotubes by treatment with several compositions of the invention and/or Dexa, as described in the following Example 2, wherein the three modulators have different concentrations.
Figure 10B:
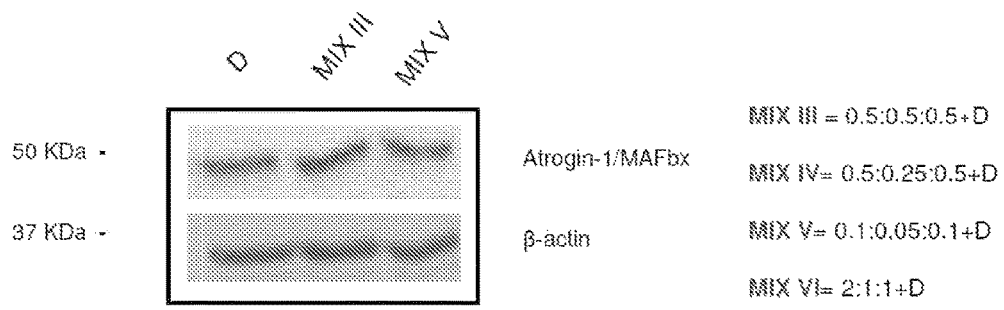
Figure 10C:
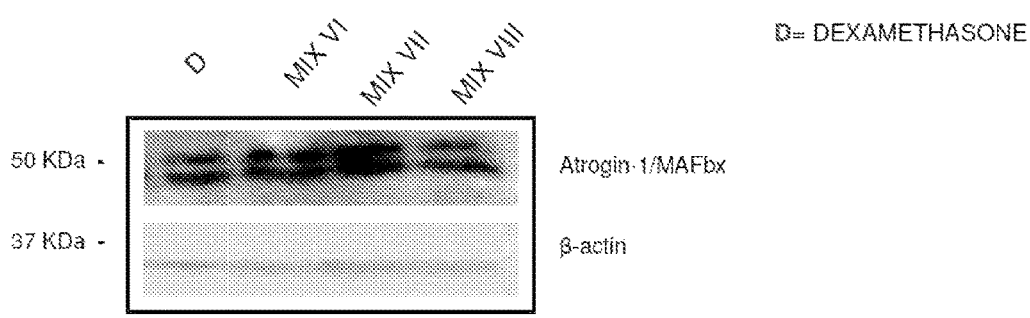
Figure 10D:
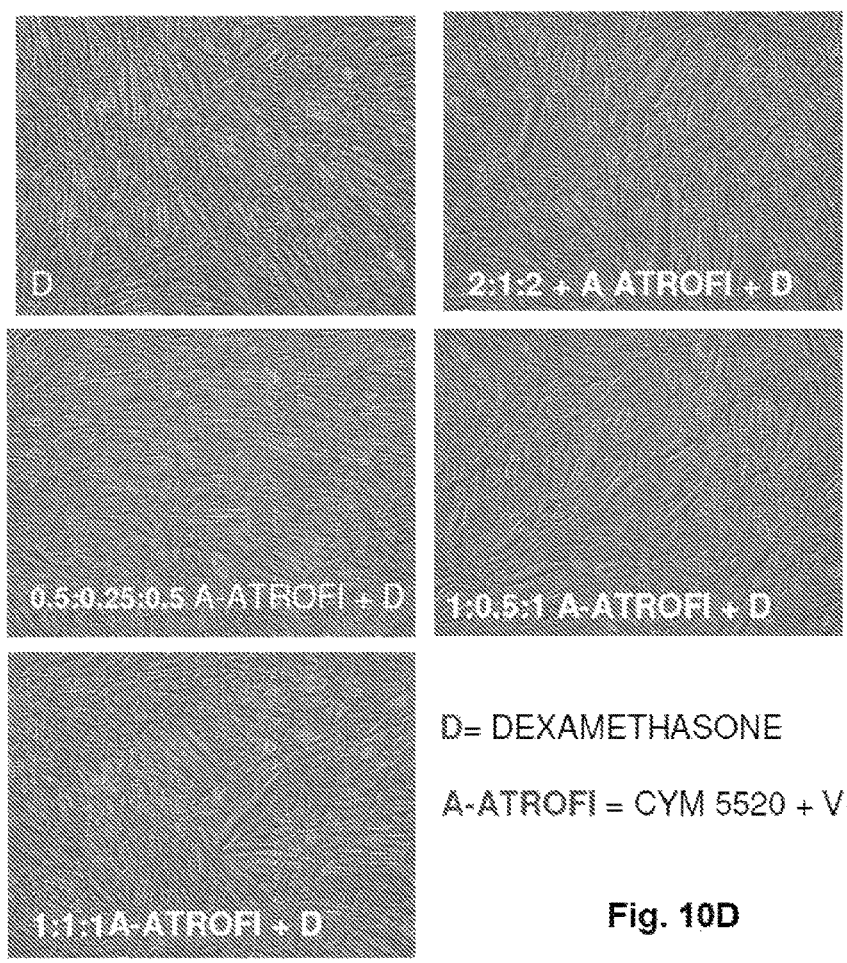
FIG. 10D shows the images of phase contrast microscope of C2C12 cells in the experiments described in the following Example 2, for the compositions of the invention subject of the graph in FIG. 10A.

The C2C12 myotubes were grown on a coverslip and, when confluent, were moved onto a medium for the differentiation for 4 days. The cells were treated with the above reported combination of the three S1PR modulators before being incubated with Dexa for 48 hours. Then, the cells were fixed and observed with microscope. The images in FIG. 10B are representative of separated experiments with similar results. To be noted is the reduced diameter of the myotubes and the number of myonuclei in the cell treated with the atrophic inducer Dexa with respect to the control and the significant effect of the treatment with the combination A-ATROFI with respect to Dexa and to the other composition of the three modulators.

Figure 11A:
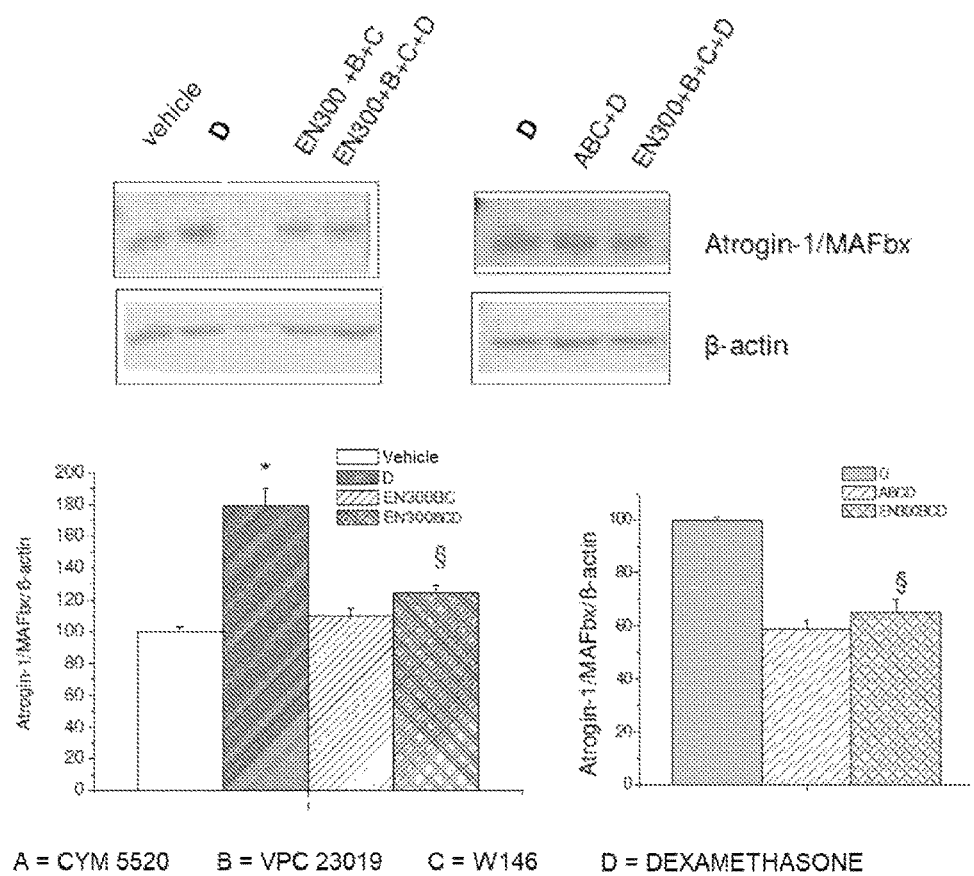
FIG. 11A shows the expression of Atrogin-1/MAFbx in C2C12 myotubes by treatment with a composition of the invention comprising EN300 as S1PR1 modulator, and/or with Dexa as described in the following Example 2.
Figure 11B:
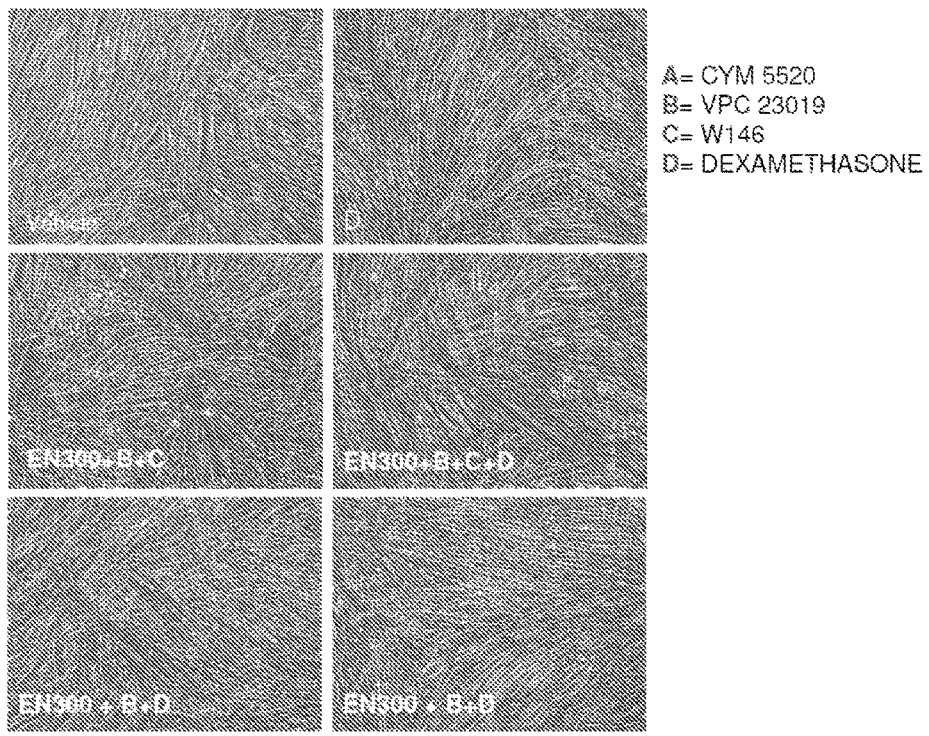
FIGS. 11B and 11B show images of phase contrast microscope of C2C12 cells in the experiments described in the following Example 2, after treatment with several compositions of the invention comprising EN300 as S1PR2 modulator and/or with Dexa.
Figure 12B:
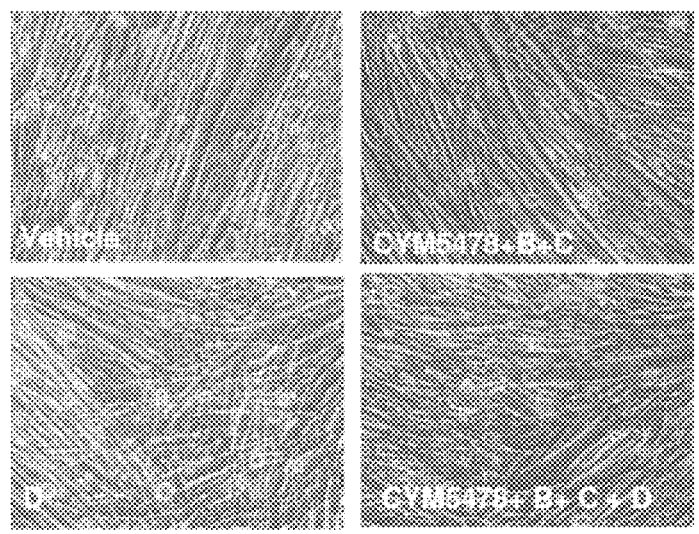
FIGS. 12B and 12C show images of phase contrast microscope for the C2C12 cells in the experiments described in the following Example 2, after treatment with various compositions of this invention comprising CYM5478 as S1PR2 modulators and/or with Dexa.
Figure 12C:
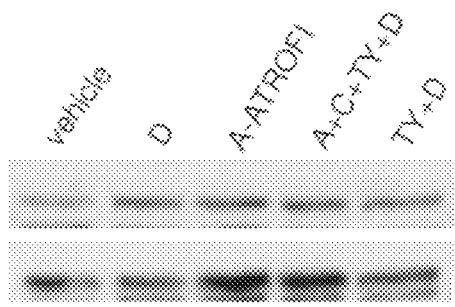
Figure 13A:
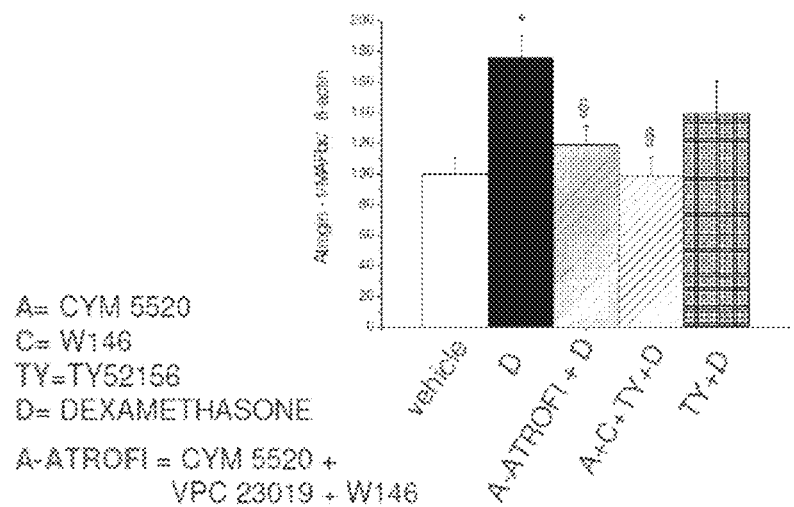
FIG. 13A shows the expression of Atrogin-1/MAFbx in C2C12 myotubes by treatment with a composition of the invention comprising TY52156 as S1PR3 modulator instead of VPC23019 and/or with Dexa.
Figure 13B:
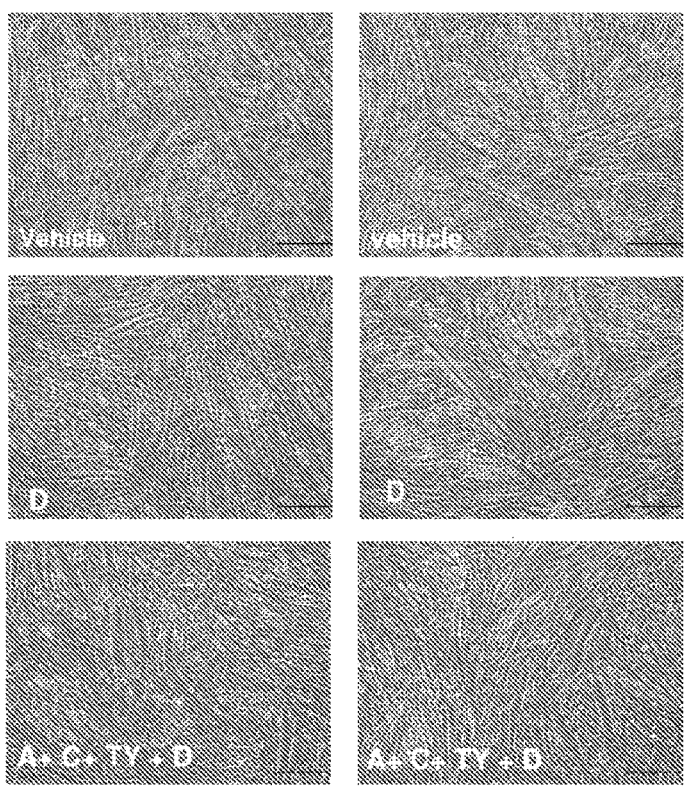
FIG. 13B show images of phase contrast microscope for the C2C12 cells in the experiments described in the following Example 2, after treatment with several compositions of this invention comprising TY52156 as S1PR3 modulators instead of VPC23019 and/or with Dexa.

Involvement of the Modulators of S1PR in Regulating the Expression of Atrogin-1/MAFbx and in Acquiring an Atrophic Phenotype in C2C12 Myotubes The efficiency of the present composition was proved also changing the structure of the molecule having an agonist/antagonist role for S1PRs, i.e. CYM5520, replaced here with EN300 and with CYM5478. As shown in the FIG. 11, the treatment in the presence of Dexa with EN300 (2 microM) leads to an effect comparable to that obtained with the combination of the invention as far as both the cellular morphology and the expression of Atrogin-1/MAFbx are concerned. Similarly, the treatment in the presence of Dexa with the compound CYM5478 (2 μM) leads to an effect comparable with that obtained with the combination of the invention, as far as both the cellular morphology and the expression of Atrogin-1/MAFbx are concerned (FIG. 12).

The conclusion is therefore that the protective effect towards agents inducing atrophy such as Dexa is obtained with the composition of the invention.

Example 3

Involvement of S1PR Modulators in Regulating the Expression of Atrogin-1/MAFbx and in Acquiring an Atrophic Phenotype in C2C12 Myotubes The efficiency of the present composition was proved also changing the way of reduction of signalling through the silencing of the expression of the S1PR3 receptor by using a short interference RNA (siRNA) specific for the mouse S1PR3. Under these experimental conditions, the incubation with S1PR3-siRNA was able to reduce the expression of the protein by 40%. Therefore, by using the composition of the invention containing the S1PR2 agonist, CYM5520, the S1PR1 antagonist, W146, and siRNA-S1PR3-siRNA, as shown in the FIG. 14, the treatment in the presence of Dexa has brought to an effect comparable to that obtained with the combination of the invention tested in Example 2 as far as both the cellular morphology and the expression of Atrogin-1/MAFbx are concerned.

Figure 16:
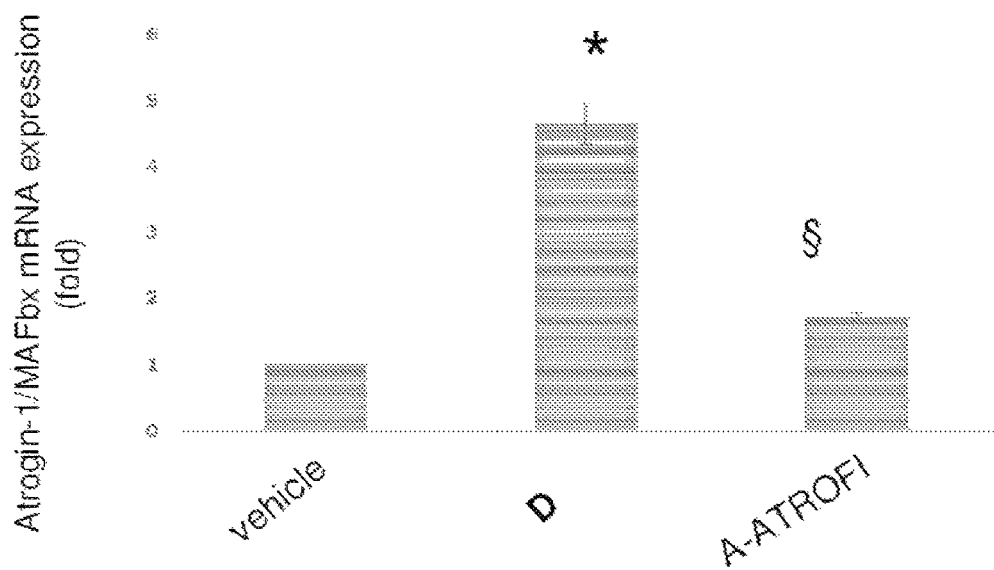
FIG. 16 shows a graph of the mRNA expression of Atrogin-1/MAFbx in atrophic C2C12 myotubes for the composition A-ATROFI of the invention and/or with Dexa.

Involvement of the Composition of the Invention in Regulating the Expression of the mRNA of Atrogin-1/MAFbx The effect of the combination A-ATROFI of the invention, as defined above, in preventing the cellular atrophy was evaluated not only on the expression of Atrogin-1/MAFbx at the protein level but also at the mRNA level. The total RNA obtained from C2C12 myotubes treated with control (vehicle treated) or dexamethasone (100 μM) (Dexa) or combination A (A-ATROFI) (the combination of the three S1PR modulators CYM5520 (2 μM) and VPC23019 (1 μM) and W146 (2 μM)) before dexamethasone (D, Dexa) for 48 hours. The total RNA was retro-transcripted as described above in the paragraph Methods. The Real Time PCR was carried out by using specific forward and reverse primers for Atrogin-1/MAFbx. The data are presented as variations of the number of times (mean±SEM) of at least three independent experiments (Student t-test, *P<0.05 versus control; § p<0.05 vs Dexa). As shown in the FIG. 16, the combination A-ATROFI of the invention has completely prevented the transcription of mRNA of the atrophic marker Atrogin-1/MAFbx.

Involvement of the Composition of the Invention in Regulating the Expression of miRNA In several models of tissue atrophy the miRNAs appear up-regulated or down-regulated. For example, the absence of weight caused by spaceflights leads to a reduction of the dimensions and strength of the skeletal muscle tissue and, under this condition, the expression of over 200 miRNA, in the gastrocnemius of mice subjected to an 11-days long spaceflight, has significantly changed and amongst them, miR-1 and miR-133a have had a decreasing trend. In addition, in the model of muscular atrophy caused by inactivity, miR-1 and miR-133a in the tissues of *Vastus lateralis* were reduced by about 10%. Muscular atrophy in the amyotrophic lateral sclerosis (ALS) is obtained with a significant increase of miR-206 (ALS murine model). Moreover, miR-206 and miR-21 were recently described as having a role in muscular wasting under catabolic conditions and increased in a murine model of Dexa-induced cartilage damage.

Figure 17:
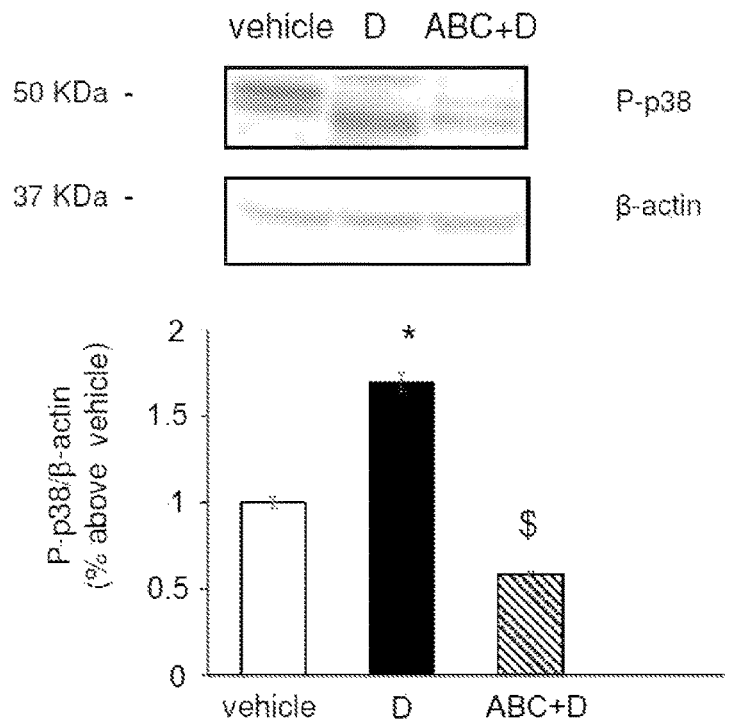
FIG. 17 shows the graph of the expression of phospho p38MAPK (p-p38 MAPK) in C2C12 myotubes for a composition of the invention and/or with Dexa.
Figure 18:
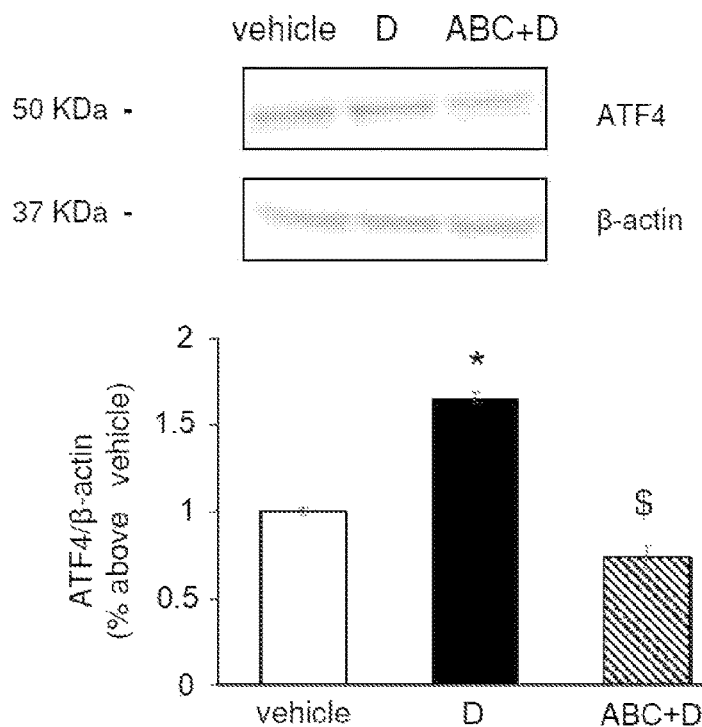
FIG. 18 shows the graph of the expression of AFT4 in C2C12 myotubes for a composition of the invention and/or with Dexa.

In particular, the combination A-ATROFI of the present invention, as defined above, is able to affect the level of expression of miR-133 and of miR-206. Cell lysates (40 μg) obtained from C2C12 myotubes treated with the vehicle (DMSO at concentration <0.05%) or with the combination of the three S1PR modulators (2 μM CYM5520 and 1 μM VPC23019 and 2 μM W146) before the control with DMSO as vehicle (less than 0.1% of final concentration) or dexamethasone (100 μM) (D, Dexa) for 48 hours, were analysed. The detection of the proteins was carried out as in FIG. 3 by Western Blotting analysis using specific anti-fosfo-p38 MAPK or anti-ATF4 antibodies. The data (mean±SEM) normalized to the β-actin band are reported in the graph as percentage with respect to the vehicle DMSO set as 1 (one-way ANOVA, *p<0.05 vs control; $ p<0.05 vs Dexa). In particular, it was observed that the pre-treatment with the present combination A-ATROFI induced a significant decrease of miR-133 (approximately 70%) and a slight increase of miR-206 at the mRNA level (approximately 40%) in a C2C12 myotube treated with Dexa, with respect to the control cells. The results are reported in the FIGS. 17 and 18.

Involvement of the Composition of the Invention in the Stress Regulation on the Protein Kinase Activated by the p38 Mitogen (p38 MAPK) and ATF4

The effect of the combination A-ATROFI of the present invention, as defined above, was determined on two targets downstream, strictly correlated to the cellular stress: the p38 mitogen (p38-MAPK)-activated protein kinase, identified as mediator of the catabolic signalling in the skeletal muscle, and ATF4.

Figure 14A:
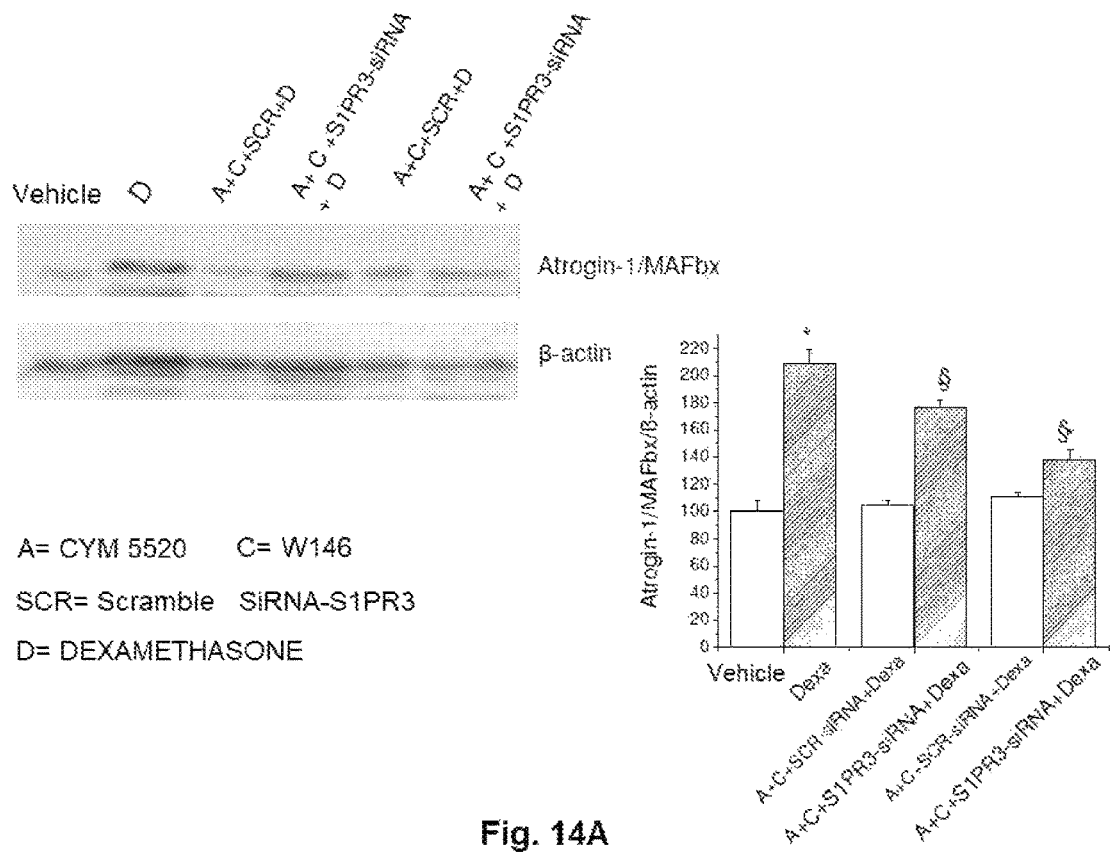
FIG. 14A shows the representative result of the Western Blotting analysis and the graph of the densitometric analysis for the expression of Atrogin-1/MAFbx in C2C12 myotubes by treatment with a composition of the invention comprising the modulators of S1PR1 (W146) and S1PR2 (CYM5520) receptors and with short interference RNA (siRNA) specific for the S1PR3 (siRNA-S1PR3) receptor instead of VPC23019 or TY52156, as modulator of the expression of S1PR3 and/or with Dexa.
Figure 14B:
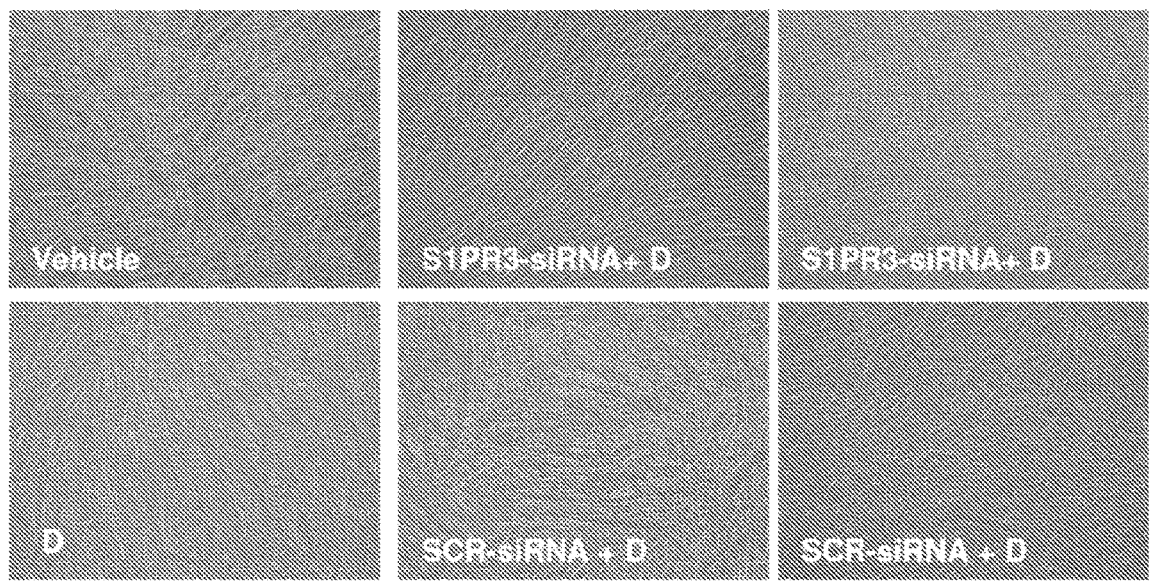
FIGS. 14B and 14C show images of phase contrast microscope for the C2C12 cells in the experiments described in the following Example 3, after treatment with a composition of this invention comprising the modulators of S1PR1 (W146) and S1PR2 (CYM5520) receptors and with short interference RNA (siRNA) specific for the S1PR3 (siRNA-S1PR3) receptor instead of VPC23019 or TY52156, as modulator of the expression of S1PR3 and/or with Dexa.
Figure 14C:
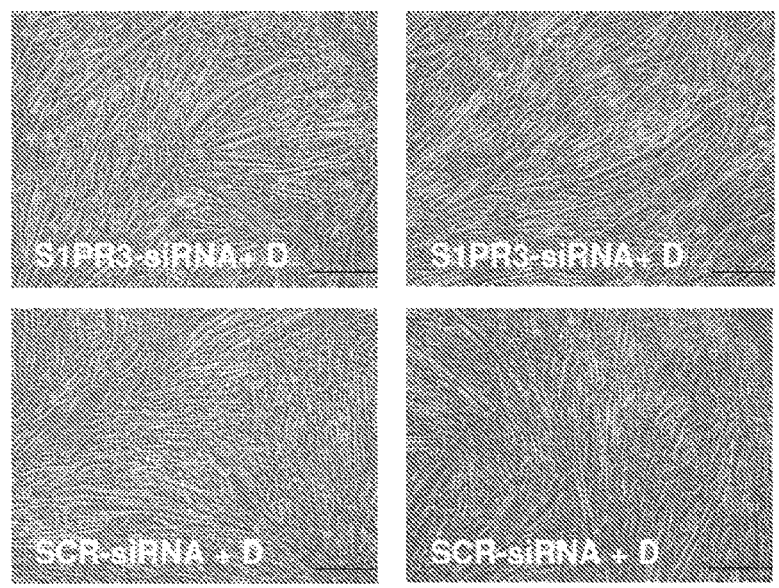
Figure 15:
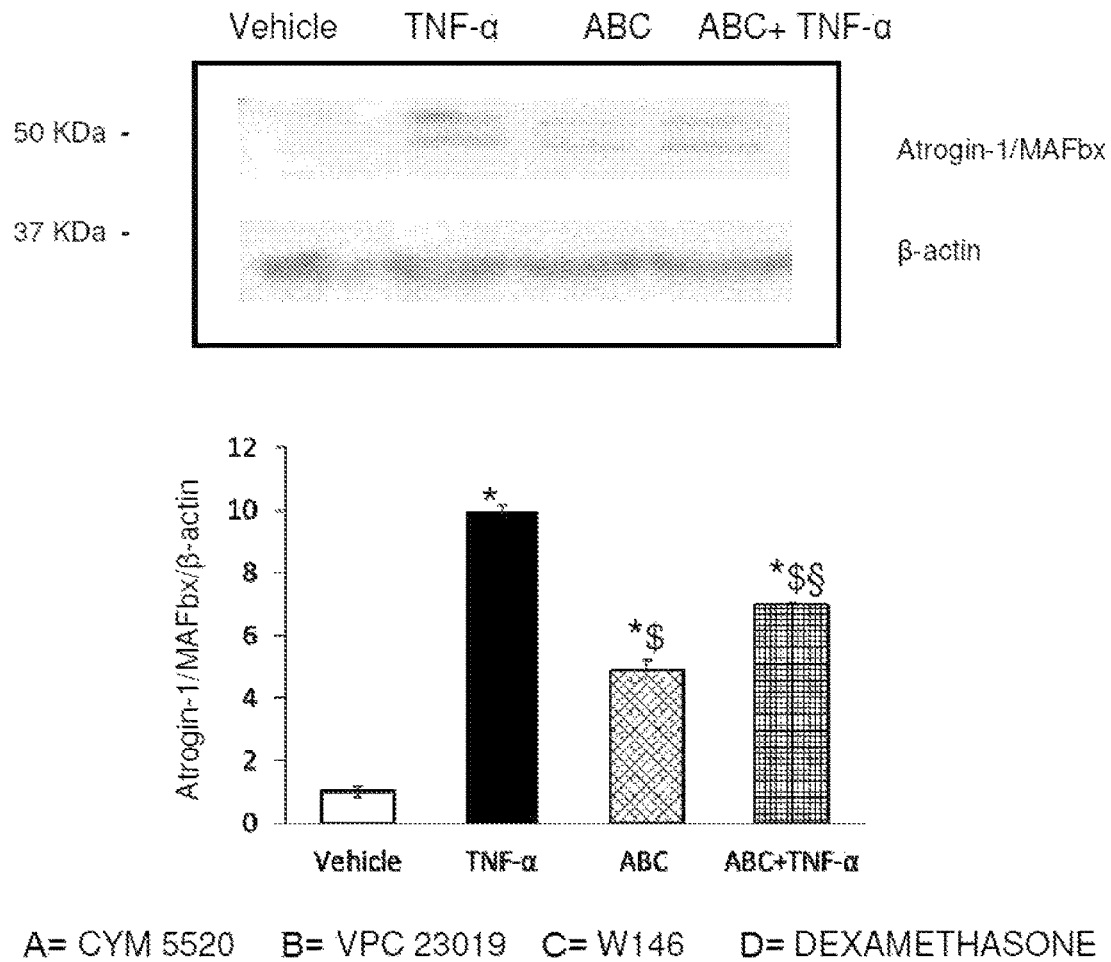
FIG. 15 shows the expression of Atrogin-1/MAFbx in C2C12 myotubes by treatment with a composition of the invention comprising and/or with Tumour Necrosis Factor alfa (TNFα).

Recent papers indicate that some forms of muscular atrophy require the activation of the transcription factor 4, also known as ATF4 a critical component, of the subunit inducible by the transcription factor bZIP stress-induced, in a complex and misunderstood molecular signalling network that causes muscle atrophy during aging, fasting and immobilization. (Adams C M et al., *Curr Opin Clin Nutr Metab Care*. 2017). The expression of ATF4 in skeletal muscle fibres is sufficient to induce muscle fibres atrophy and necessary for muscle atrophy under various stress conditions, including aging, fasting and limb immobilization. As shown in FIGS. 14 and 15, the expression of the two signalling molecules was significantly impaired by Dexa and the pre-treatment with the A-ATROFI combination of the invention has restored its baseline level.

Involvement of the Composition of the Invention in the Response of Myoblasts in the Presence of a Factor Inducing Muscular Atrophy (Dexa)

The C2C12 myoblasts represent the non-differentiated precursors of myotubes and of muscular fibre; they were grown in a plate at 40% confluence and treated as reported in FIG. 9. After 24 hours of incubation, the cells were collected and processed for the analysis with the TALI cytometer. As evident from the cytometric analysis, the treatment with the A-ATROFI combination induces an arrest of the cells in the phase of the cellular cycle called G0G1 and protects cells from death by apoptosis (cellular fraction in the phase apoptosis or subG0).

Figure 19:
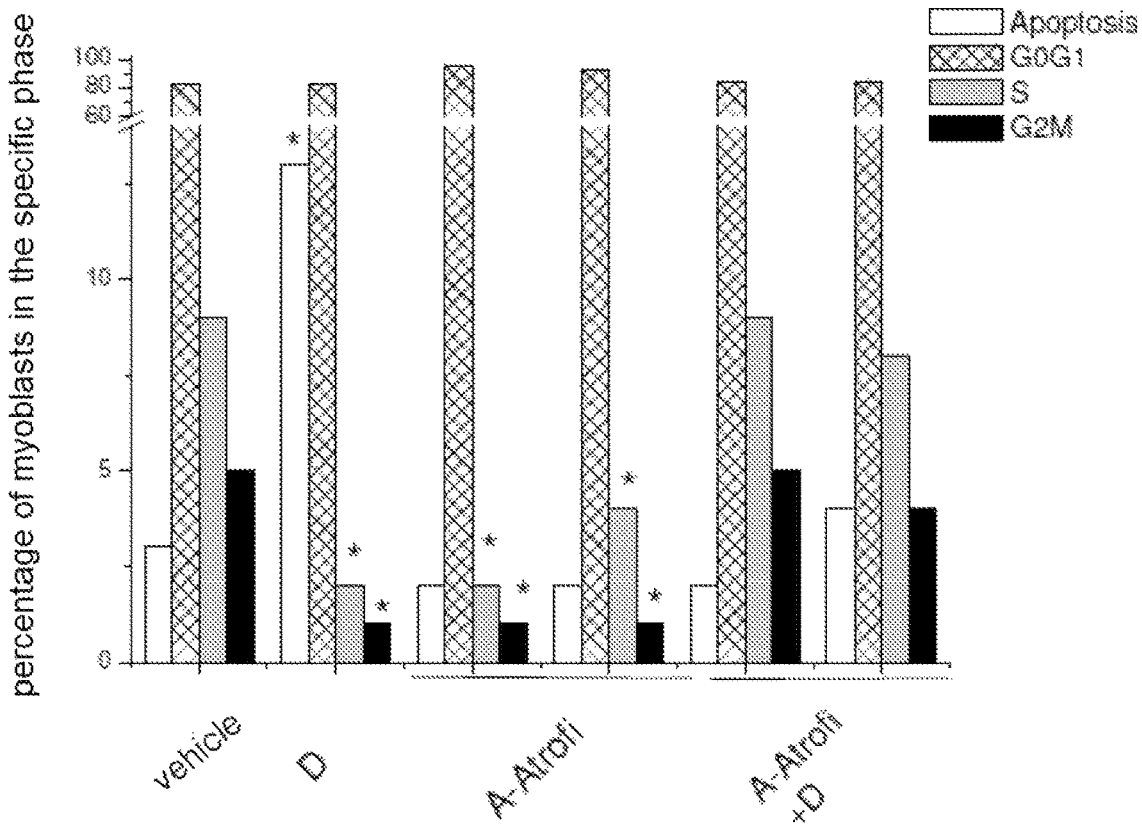
FIG. 19 shows in a graph the effect of the invention composition and/or with Dexa on the percentage of myoblasts in the specific phase of the cellular cycle.
Figure 20A:
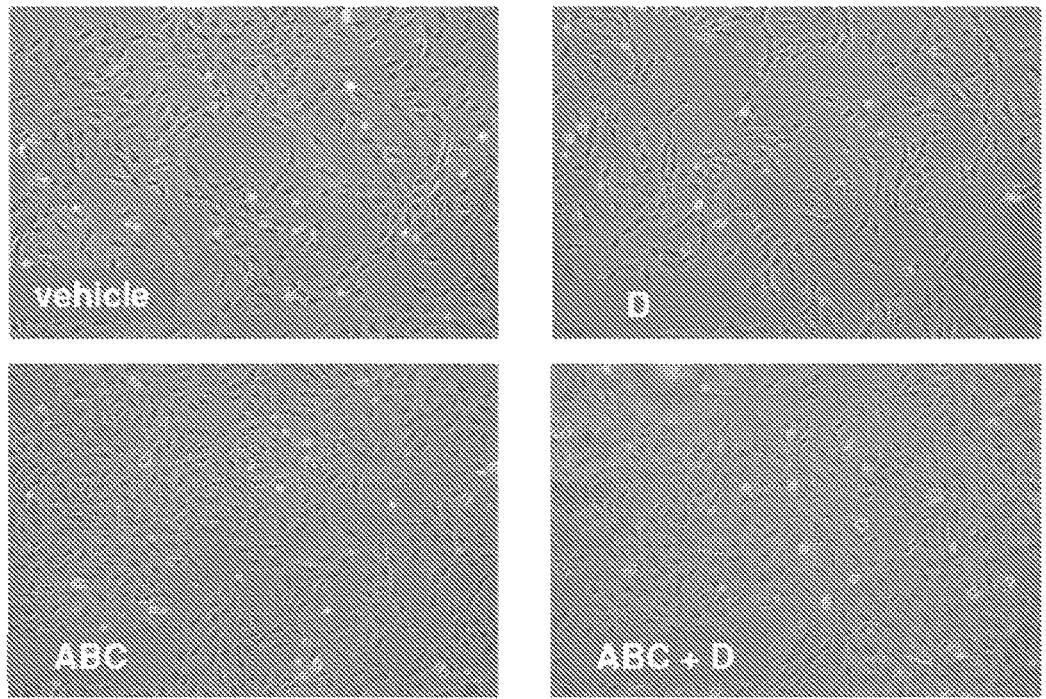
FIGS. 20A and 20B show the images of phase contrast microscope showing the effect of the invention composition and/or with Dexa on the morphology and the cellular growth of C2C12 myoblasts.
Figure 20B:
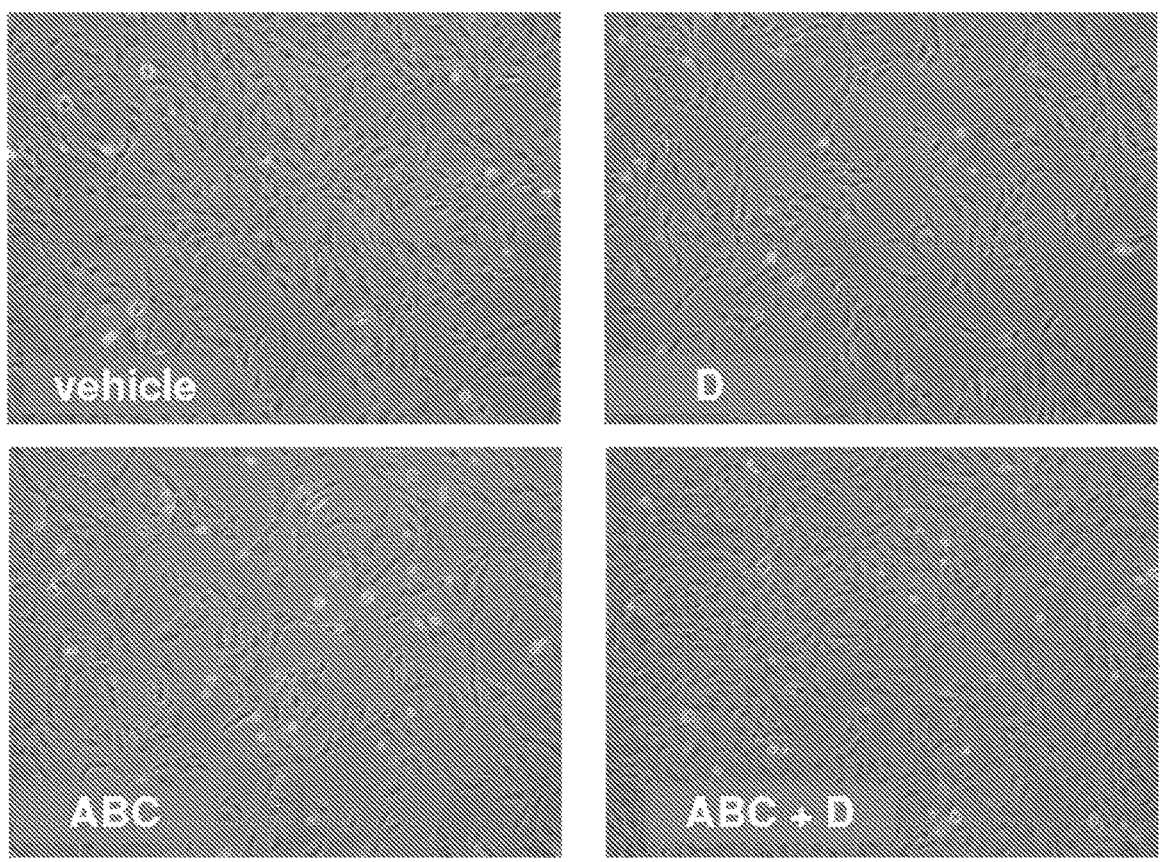

As visible from the images in FIGS. 20, these cells are smaller and not multinucleated. The cells were treated at 40% of their confluence and treated as in FIG. 7. After 24 hours of incubation, the cells were visualised and analysed under the microscope. The images are representative of two separate experiments with similar results. Notable is the reduced cell growth in the cells treated with the combination of compounds (A-ATROFI) in the presence of Dexa compared to the sole treatment with Dexa. The data obtained by cytometry experiments are shown in graph (FIG. 19), while the morphology is illustrated in the subsequent figures (FIGS. 20A and 20B).

Therefore, the combination of this invention can be used not only as a mixture protecting against atrophy the differentiated cell but also in the context of the muscular precursors damaged by the presence of glucocorticoids. The arrest in G0 and the reduction in the number of cells in apoptosis indicates that the combination of the invention provides resistance to cellular precursors of the skeletal muscle.

The invention claimed is:

1. A pharmaceutical composition comprising:
a compound of formula (I)

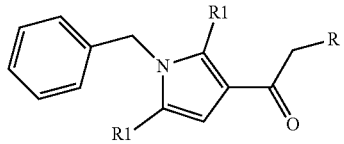

(I)

wherein R is selected from the group consisting of chlorine, 6-oxo-1,6-dihydro-pyridin-3-carbonitrile, and 6-oxo-1,6-dihydro-pyridin-3-trifluoromethyl; and R1 is independently selected from the group consisting of H, (C1-C4)alkyl, —CH$_2$-phosphate, and phosphate;
(3R)-3-amino-4-[(3-hexylphenyl)amino]-4-oxobutyl]-phosphonic acid (W 146), and
a compound selected from [2-amino-2-(3-octyl-phenyl-carbamoyl)-ethyl] ester of phosphoric acid (VPC 23019), 2-(4-chlorophenyl) hydrazide of N-(4-chlorophenyl)-3,3-dimethyl-2-oxobutanimidic acid (TY52156), and a molecule siRNA of SEQ ID NO:1,
or pharmaceutically acceptable salts thereof, and a pharmaceutically acceptable excipient and/or salt thereof.

2. The pharmaceutical composition of claim 1, wherein in said compound of formula (I) R1 is methyl.

3. The pharmaceutical composition of claim 2, wherein in said compound of formula (I) R is selected from the group consisting of chlorine (EN300), 6-oxo-1,6-dihydro-pyridin-3-carbonitrile (CYM5520), and 6-oxo-1,6-dihydro-pyridin-3-trifluorometile (CYM5478).

4. The pharmaceutical composition of claim 1, further comprising one or more further active principles.

5. The pharmaceutical composition of claim 1, comprising a concentration for each of said compounds of formula (I), W 146, and compound selected from VPC23019, TY52156 and siRNA of SEQ ID NO: 1 ranging between 0.1 µM and 5 µM.

6. The pharmaceutical composition of claim 5, comprising said compound of formula (I) and W146 in equal concentration, to which is added a concentration of said compound selected from VPC23019, TY52156 and siRNA of SEQ ID NO: 1 equal to about half of the concentration of each of the other two components.

7. The pharmaceutical composition of claim 6, comprising said compound of formula (I), VPC23019 and W146 in the following concentration: 2 µM of compound (I)+1 µM of VPC23019+2 µM of W146.

8. A method, for the prevention and treatment of atrophy or of degeneration of skeletal muscle or of sarcopenia, comprising administering an effective amount of a pharmaceutical composition of claim 1 to a patient in need thereof.

9. The method of claim 8, wherein said atrophy and/or degeneration of skeletal muscle is caused by a pathology selected from the group consisting of heart failure, cancer, chronic renal failure, chronic pulmonary failure, and by a glucocorticoid- or cytokine-dependent pathology.

* * * * *

```
                        SEQUENCE LISTING

<160> NUMBER OF SEQ ID NOS: 5

<210> SEQ ID NO 1
<211> LENGTH: 19
<212> TYPE: RNA
<213> ORGANISM: Artificial Sequence
<220> FEATURE:
<223> OTHER INFORMATION: short interfering RNA

<400> SEQUENCE: 1
cgggguccuc ugcaaguga                                                19

<210> SEQ ID NO 2
<211> LENGTH: 20
<212> TYPE: RNA
<213> ORGANISM: Artificial Sequence
<220> FEATURE:
<223> OTHER INFORMATION: direct primer

<400> SEQUENCE: 2
gcagccaaga agagaaagaa                                               20

<210> SEQ ID NO 3
<211> LENGTH: 19
<212> TYPE: RNA
<213> ORGANISM: Artificial Sequence
<220> FEATURE:
<223> OTHER INFORMATION: forward primer

<400> SEQUENCE: 3
ctgtgacttt gctatcagc                                                19

<210> SEQ ID NO 4
<211> LENGTH: 21
<212> TYPE: RNA
<213> ORGANISM: Artificial Sequence
<220> FEATURE:
<223> OTHER INFORMATION: direct primer
```

```
<400> SEQUENCE: 4
ggcaaattca acggcacagt c                                        21

<210> SEQ ID NO 5
<211> LENGTH: 19
<212> TYPE: RNA
<213> ORGANISM: Artificial Sequence
<220> FEATURE:
<223> OTHER INFORMATION: forward primer

<400> SEQUENCE: 5
tcgctcctgg aagatggtg                                           19
```